United States Patent [19]

Andreas et al.

[11] Patent Number: 6,036,699
[45] Date of Patent: Mar. 14, 2000

[54] DEVICE AND METHOD FOR SUTURING TISSUE

[75] Inventors: Bernard H. Andreas, Fremont; James W. Vetter, Portola Valley, both of Calif.

[73] Assignee: Perclose, Inc., Menlo Park, Calif.

[21] Appl. No.: 08/824,031

[22] Filed: Mar. 26, 1997

Related U.S. Application Data

[63] Continuation-in-part of application No. 08/259,410, Jun. 14, 1994, Pat. No. 5,779,719, and a continuation-in-part of application No. 08/252,124, Jun. 1, 1994, Pat. No. 5,613,924, said application No. 08/259,410, is a continuation-in-part of application No. 07/989,611, Dec. 10, 1992, Pat. No. 5,417,699.

[51] Int. Cl.⁷ .................................................. A61B 17/04
[52] U.S. Cl. ........................... 606/139; 606/144; 606/148
[58] Field of Search ................................... 606/139, 144, 606/145, 147, 148

[56] References Cited

U.S. PATENT DOCUMENTS

| 312,408 | 2/1885 | Wacker Hagen | 606/223 |
| D. 372,310 | 7/1996 | Hartnett | D24/146 |
| 659,422 | 10/1900 | Shidler . | |
| 2,397,823 | 4/1946 | Walter | 606/206 |
| 2,646,045 | 7/1953 | Priestley | 128/340 |

(List continued on next page.)

FOREIGN PATENT DOCUMENTS

| 01407557 | 5/1985 | European Pat. Off. . | |
| 0 474 887 A1 | 3/1992 | European Pat. Off. | A61B 17/00 |
| 0 478 358 A1 | 4/1992 | European Pat. Off. | A61B 17/04 |
| 0 589 409 A1 | 9/1992 | European Pat. Off. | A61B 17/04 |
| 0 624 343 A2 | 4/1993 | European Pat. Off. | A61B 17/04 |
| 0 542 126 A3 | 5/1993 | European Pat. Off. | A61B 17/04 |

(List continued on next page.)

OTHER PUBLICATIONS

Datascope Corporation, Montvale, NJ, (1991) 1 pg, American Heart Assoc. Meeting, Anaheim.
Kensey Nash Corportion, Exton, PA, "The Hemostatic Puncture Closure Device", 2 pages.
"Innovation Through Progress", REMA–Medizintechnik GmbH, Jan. 1992.
AD: The Laurus In–Line Endoscopic Suturing Device (The Laurus ND–2600 Needle Driver), Laurus Medical Corp., Rev. Oct. 1994.
Cardiac Catheterization and Angiography, 3$^{rd}$ Ed., Lea Nad Febiger, Philadelphia, 1986.
Cardio–Thoracic Systems Prospectus Dated Mar. 20, 1996.
Elgiloy Brochure, Jun. 23, 1959, Elgin National Watch Co., Elgin, IL.
Product Brochure "The Proven Solution To Endoscopic Suturing", Laurus Medical Corp., Irvine, CA Oct. 1994.

Primary Examiner—Gary Jackson
Attorney, Agent, or Firm—Townsend and Townsend and Crew LLP

[57] ABSTRACT

The present invention provides medical devices and methods for: suturing tissue by proximally drawing sutures through a tissue layer in the proximity of an aperture; suturing vascular tissue while maintaining adequate perfusion or hemostasis, or both; anastomosing a graft to an aperture in a vessel wall while maintaining hemostasis at the anastomosis with physiological flow and/or pressure in the vessel lumen; punching and removing tissue to form an aperture in a vessel wall while maintaining hemostasis at the aperture with physiological flow and/or pressure in the vessel lumen; automatically and repeatably placing suture thread through vessel wall tissue surrounding an aperture in the vessel wall in a suture pattern that is useful for anastomosing a tubular graft to the aperture; and, deploying a suture with one end extending through the tissue that surrounds a punched aperture in a vessel wall and the opposite suture end extending radially through a tubular graft wall adjacent an open end of the graft, such that a vessel anastomosis may be rapidly and repeatably performed in a CABG procedure even while the vessel is under physiological flow.

66 Claims, 15 Drawing Sheets

U.S. PATENT DOCUMENTS

| | | | |
|---|---|---|---|
| 2,959,172 | 11/1960 | Held | 128/340 |
| 3,104,666 | 9/1963 | Hale et al. | |
| 3,470,875 | 10/1969 | Johnson | 606/145 |
| 3,653,388 | 4/1972 | Tenckhoff | 128/347 |
| 3,665,926 | 5/1972 | Flores | 128/326 |
| 3,776,237 | 12/1973 | Hill et al. | 128/305 |
| 3,820,544 | 6/1974 | Semm | 606/139 |
| 3,926,194 | 12/1975 | Greenberg et al. | |
| 3,939,820 | 2/1976 | Grayzel | 128/1 |
| 4,018,228 | 4/1977 | Goosen | 128/305 |
| 4,109,658 | 8/1978 | Hughes | 128/340 |
| 4,161,951 | 7/1979 | Scanlan, Jr. | 606/145 |
| 4,168,073 | 9/1979 | LaRue | |
| 4,216,776 | 8/1980 | Downie et al. | 128/305 |
| 4,235,177 | 11/1980 | Arbuckle | 606/144 |
| 4,317,445 | 3/1982 | Robinson | 604/168 |
| 4,411,654 | 10/1983 | Boarini et al. | 604/165 |
| 4,412,832 | 11/1983 | King et al. | 606/164 |
| 4,437,465 | 3/1984 | Nomoto et al. | |
| 4,493,323 | 1/1985 | Albright et al. | 128/340 |
| 4,553,543 | 11/1985 | Amarasinghe | |
| 4,587,969 | 5/1986 | Gillis | 128/314 |
| 4,596,559 | 6/1986 | Fleishhacker | 604/170 |
| 4,629,450 | 12/1986 | Suzuki et al. | 606/104 |
| 4,738,666 | 4/1988 | Fuqua | 604/280 |
| 4,744,364 | 5/1988 | Kensey | 128/314 |
| 4,836,205 | 6/1989 | Barrett | |
| 4,852,568 | 8/1989 | Kensey | 128/325 |
| 4,890,612 | 1/1990 | Kensey | 606/213 |
| 4,898,155 | 2/1990 | Ovil et al. | |
| 4,911,164 | 3/1990 | Roth | 604/148 |
| 4,926,860 | 5/1990 | Stice et al. | 606/144 |
| 4,929,246 | 5/1990 | Sinofsky | 606/8 |
| 4,935,027 | 6/1990 | Yoon | 606/148 |
| 4,957,498 | 9/1990 | Caspari et al. | |
| 4,983,168 | 1/1991 | Moorehead | 604/161 |
| 4,984,581 | 1/1991 | Stice | 128/772 |
| 5,002,563 | 3/1991 | Pyka et al. | 606/222 |
| 5,009,643 | 4/1991 | Reich et al. | 604/165 |
| 5,021,059 | 6/1991 | Kensey et al. | 606/213 |
| 5,037,433 | 8/1991 | Wilk et al. | 606/144 |
| 5,047,039 | 9/1991 | Avant et al. | 606/148 |
| 5,059,201 | 10/1991 | Asnis | 106/148 |
| 5,061,274 | 10/1991 | Kensey | 606/213 |
| 5,100,419 | 3/1992 | Ehlers | 606/140 |
| 5,100,432 | 3/1992 | Matsutani | 606/223 |
| 5,109,780 | 5/1992 | Slouf et al. | 112/169 |
| 5,129,913 | 7/1992 | Ruppert | 606/184 |
| 5,147,373 | 9/1992 | Ferzli | 606/148 |
| 5,160,339 | 11/1992 | Chen et al. | 606/157 |
| 5,171,251 | 12/1992 | Bregen et al. | 606/157 |
| 5,192,294 | 3/1993 | Blake, III | 606/184 |
| 5,192,302 | 3/1993 | Kensey et al. | 606/213 |
| 5,219,358 | 6/1993 | Bendel et al. | 606/139 |
| 5,222,974 | 6/1993 | Kensey et al. | 606/213 |
| 5,234,443 | 8/1993 | Phan et al. | 606/148 |
| 5,242,427 | 9/1993 | Bilweis | 606/264 |
| 5,250,033 | 10/1993 | Evans et al. | 604/160 |
| 5,250,053 | 10/1993 | Snyder | 606/148 |
| 5,254,126 | 10/1993 | Filipi et al. | 606/148 |
| 5,258,003 | 11/1993 | Ciaglia et al. | 606/185 |
| 5,279,311 | 1/1994 | Snyder | 128/898 |
| 5,289,963 | 3/1994 | McGarry | 227/175 |
| 5,290,284 | 3/1994 | Adair | 606/37 |
| 5,290,297 | 3/1994 | Phillips | 606/144 |
| 5,293,881 | 3/1994 | Green et al. | 128/898 |
| 5,295,993 | 3/1994 | Green | 606/184 |
| 5,300,085 | 4/1994 | Yock | 606/191 |
| 5,304,184 | 4/1994 | Hathaway | 606/148 |
| 5,304,185 | 4/1994 | Taylor | 606/147 |
| 5,306,254 | 4/1994 | Nash et al. | 604/168 |
| 5,320,632 | 6/1994 | Heidmueller | 606/144 |
| 5,336,230 | 8/1994 | Leichtling et al. | 606/148 |
| 5,336,231 | 8/1994 | Adair | 606/148 |
| 5,342,369 | 8/1994 | Harryman, II | 606/148 |
| 5,364,408 | 11/1994 | Gordon | 606/144 |
| 5,368,601 | 11/1994 | Saver et al. | 606/144 |
| 5,374,275 | 12/1994 | Bradley et al. | 606/148 |
| 5,387,221 | 2/1995 | Bisgaard | 606/148 |
| 5,387,227 | 2/1995 | Grice | 606/222 |
| 5,395,349 | 3/1995 | Quiachon et al. | 604/248 |
| 5,397,325 | 3/1995 | Della Badia et al. | 606/144 |
| 5,403,329 | 4/1995 | Hinchcliffe | 606/147 |
| 5,403,338 | 4/1995 | Milo | 606/184 |
| 5,411,481 | 5/1995 | Allen et al. | 606/139 |
| 5,417,699 | 5/1995 | Klein et al. | 606/144 |
| 5,425,705 | 6/1995 | Evard et al. | 604/28 |
| 5,431,666 | 7/1995 | Sauer et al. | 606/139 |
| 5,433,700 | 7/1995 | Peters | 604/4 |
| 5,452,733 | 9/1995 | Sterman et al. | 128/898 |
| 5,454,834 | 10/1995 | Boebel et al. | 606/228 |
| 5,458,574 | 10/1995 | Machold et al. | 604/101 |
| 5,476,469 | 12/1995 | Hathaway | |
| 5,478,309 | 12/1995 | Sweezer et al. | 604/4 |
| 5,486,190 | 1/1996 | Green | 606/184 |
| 5,489,295 | 2/1996 | Piplani et al. | 623/1 |
| 5,496,332 | 3/1996 | Sierra et al. | 606/139 |
| 5,507,744 | 4/1996 | Tay et al. | 606/50 |
| 5,507,755 | 4/1996 | Gresl et al. | 606/139 |
| 5,507,757 | 4/1996 | Sauer et al. | 606/144 |
| 5,509,902 | 4/1996 | Raulerson | 604/175 |
| 5,520,655 | 5/1996 | Davila et al. | 604/167 |
| 5,527,322 | 6/1996 | Klein et al. | 606/144 |
| 5,540,704 | 7/1996 | Gordon et al. | 606/144 |
| 5,545,171 | 8/1996 | Sharkey et al. | 606/148 |
| 5,545,178 | 8/1996 | Kensey et al. | 606/213 |
| 5,545,180 | 8/1996 | Le et al. | 606/232 |
| 5,562,686 | 10/1996 | Sauer et al. | 606/144 |
| 5,562,728 | 10/1996 | Lazarus et al. | 623/1 |
| 5,573,540 | 11/1996 | Yoon | 606/144 |
| 5,591,179 | 1/1997 | Edelstein | 606/144 |
| 5,611,794 | 3/1997 | Sauer et al. | 606/8 |
| 5,613,975 | 3/1997 | Christy | 606/144 |
| 5,836,956 | 11/1998 | Buelna et al. | 606/148 |
| 5,846,253 | 12/1998 | Buelna et al. | 606/148 |

FOREIGN PATENT DOCUMENTS

| | | | |
|---|---|---|---|
| 0 568 098 A2 | 11/1993 | European Pat. Off. | A61B 17/04 |
| 4210724 C1 | 7/1983 | Germany . | |
| 405042161 | 2/1993 | Japan | 606/148 |
| 1093 329 | 5/1984 | Russian Federation . | |
| 1174 036 | 8/1985 | Russian Federation . | |
| 820810 | 6/1979 | U.S.S.R. | 606/148 |
| 993922 | 2/1983 | U.S.S.R. | 606/148 |
| 1648400 | 5/1991 | U.S.S.R. | 606/148 |
| WO 95/35065 | of 0000 | WIPO . | |
| WO 94/27503 | 6/1993 | WIPO | A61B 17/00 |
| WO 94/28801 | 6/1993 | WIPO | A61B 17/04 |
| WO 95/05121 | 8/1993 | WIPO | A61B 17/04 |
| 9405213 | 3/1994 | WIPO . | |

FIG. 8
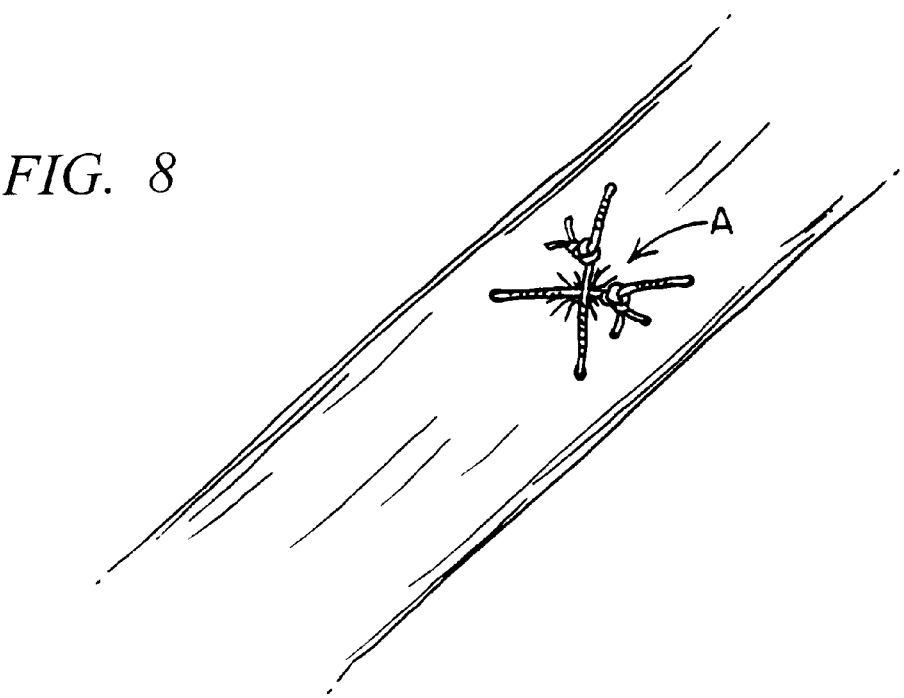
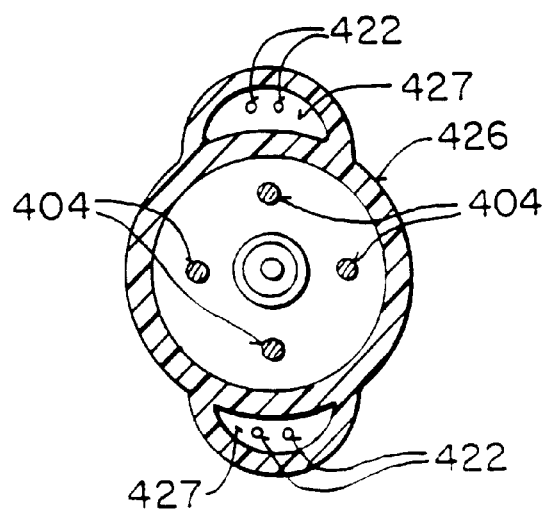
FIG. 3

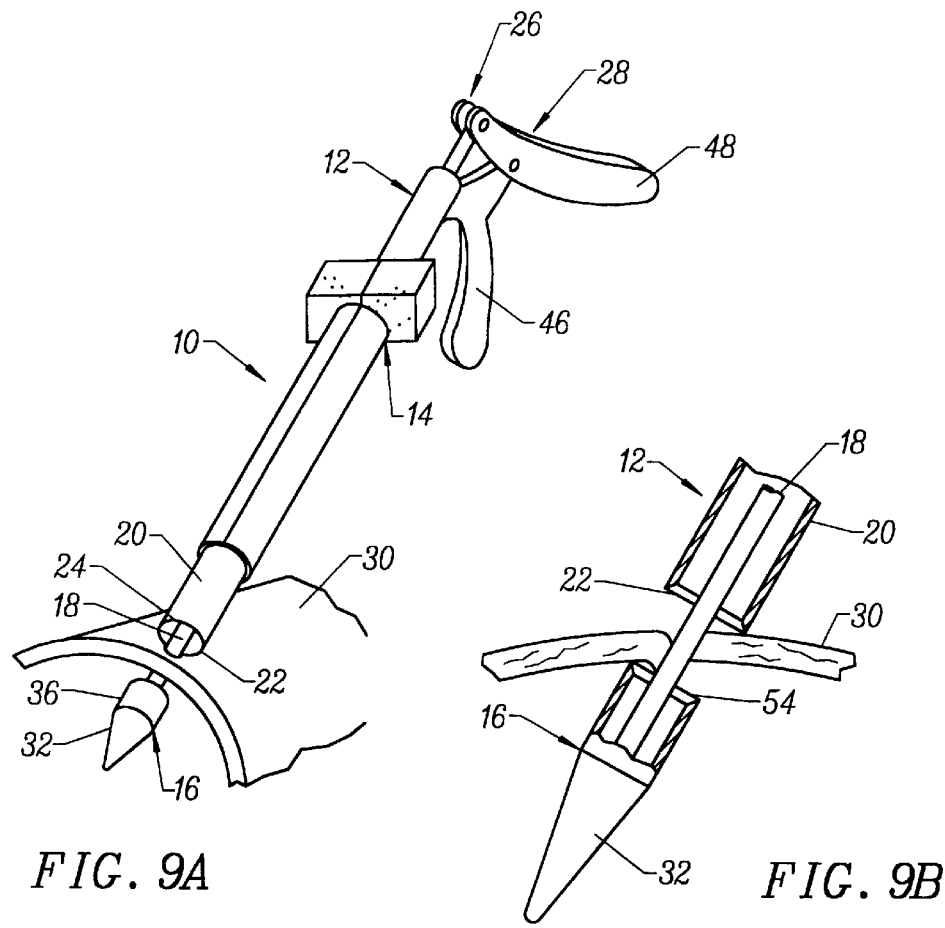
FIG. 9A
FIG. 9B
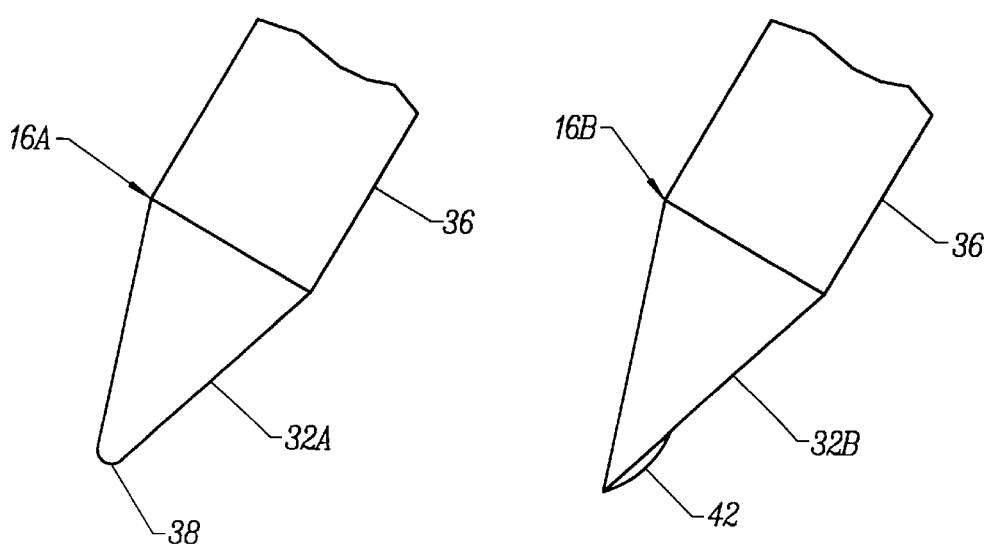
FIG. 10A
FIG. 10B

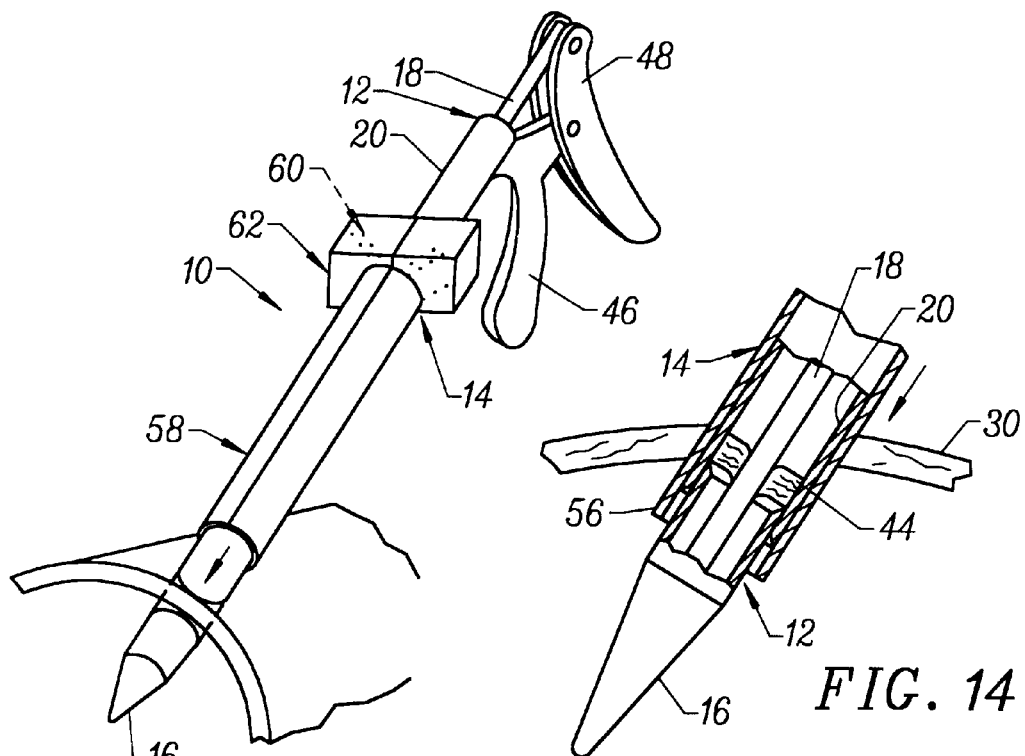
FIG. 13
FIG. 14
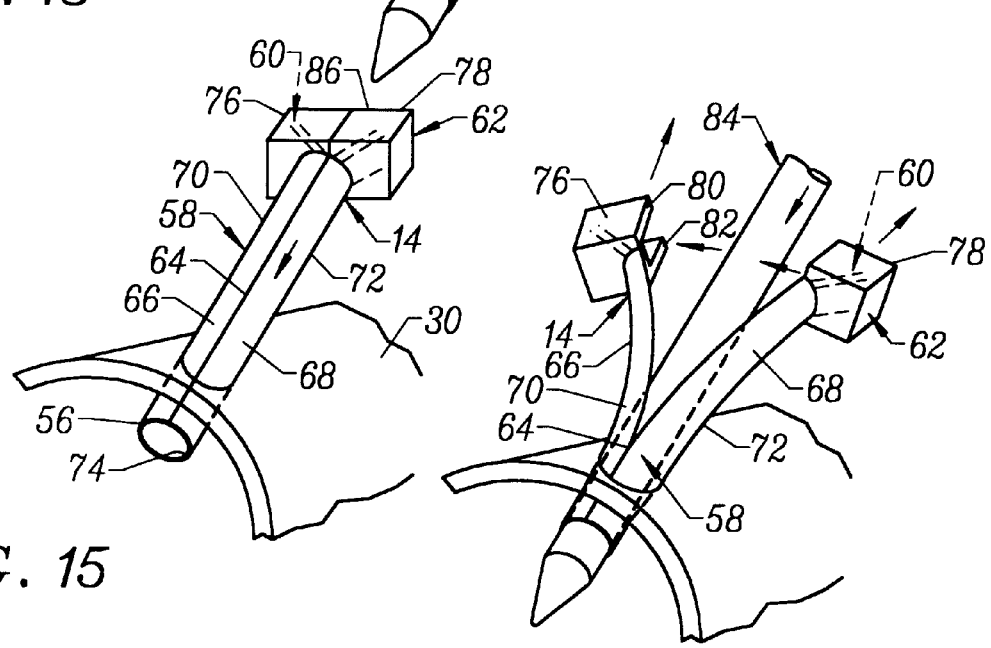
FIG. 15
FIG. 16

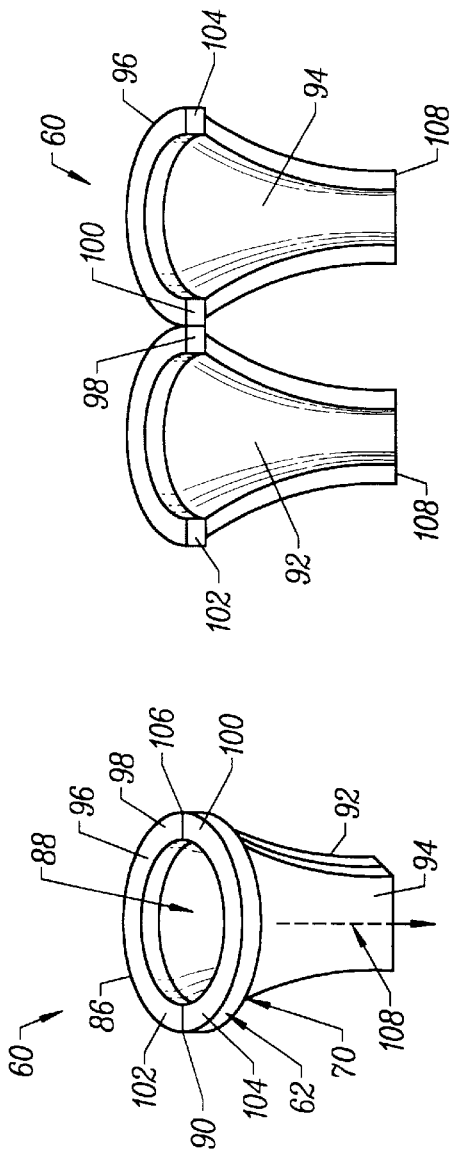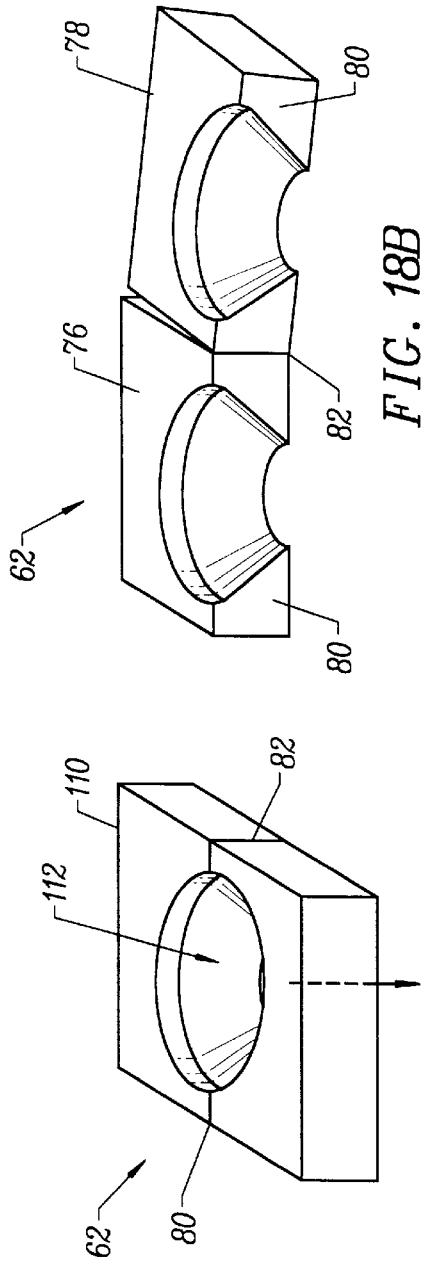

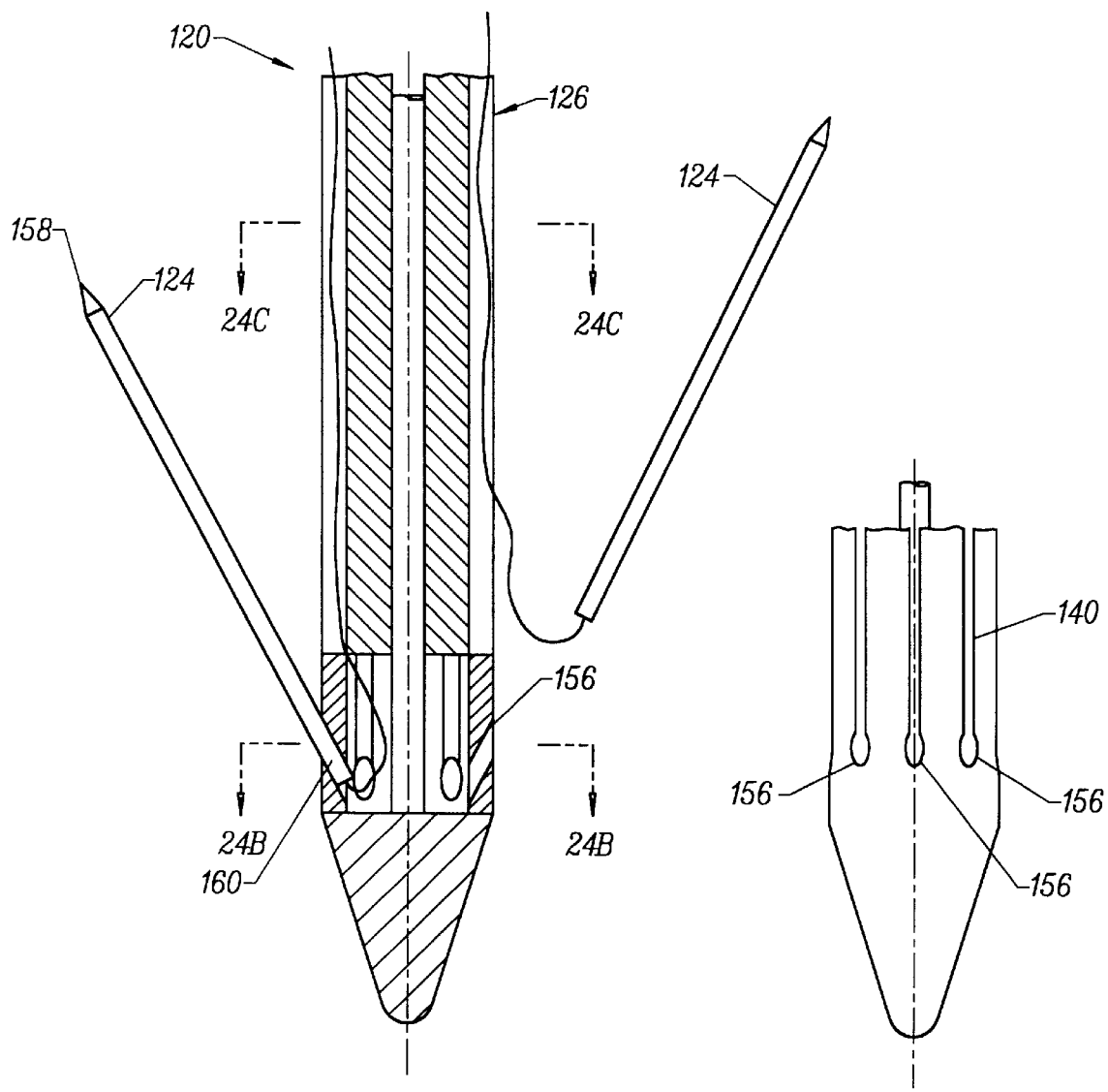

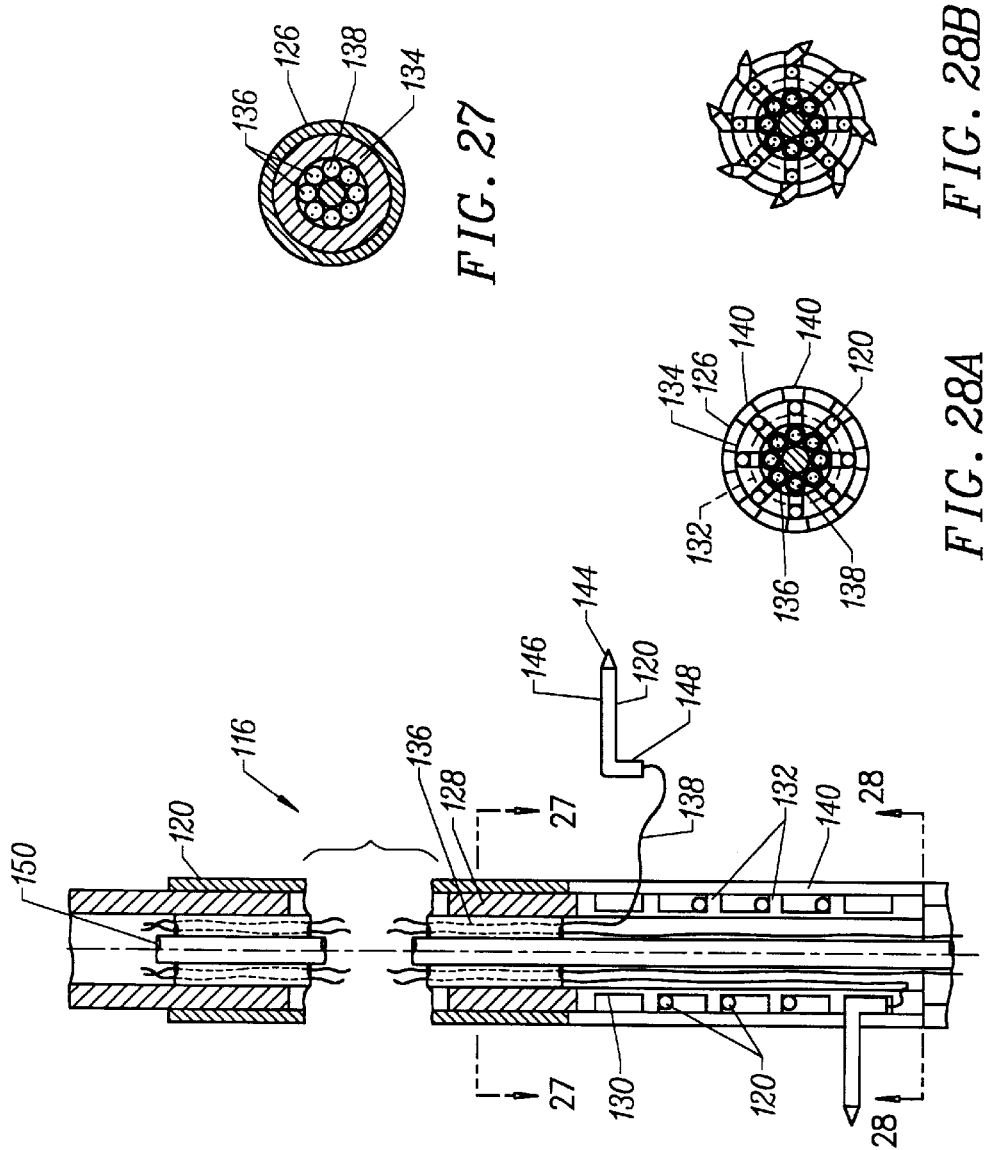

DEVICE AND METHOD FOR SUTURING TISSUE

RELATED APPLICATIONS

The present invention repeats a substantial portion of application Ser. No. 07/989,611, filed Dec. 10, 1992, now issued as U.S. Pat. No. 5,417,699, which is relied on for priority by continuation-in part application Ser. No. 08/252,124, filed Jun. 1, 1994, and continuation-in-part application Ser. No. 08/259,410, filed Jun. 14, 1994 now U.S. Pat. No. 5,779,719. The present application claims disclosure presented in the prior applications, as well as, adds and claims additional disclosure not presented in the prior applications. Since the present application names an inventor named in the prior application, it may constitute a continuation-in-part of the prior applications. These prior applications are incorporated fully herein by reference.

FIELD OF THE INVENTION

The present invention relates generally to devices and methods for the suturing of tissue in various applications such as closure of arterial and venous puncture sites, suturing a graft anastomosis to an aperture in a vessel wall or other types of tissue, and the like. More particularly, the inventive devices and methods provide for suturing the tissue of a vessel even though the vessel may be under physiological flow and while preferably maintaining hemostasis.

BACKGROUND OF THE INVENTION

A number of diagnostic and interventional vascular procedures are now performed transluminally, where a catheter is introduced to the vascular system at a convenient access location and guided through the vascular system to a target location using established techniques. Such procedures require vascular access which is usually established using the well known Seldinger technique, as described, for example, in William Grossman's "Cardiac Catheterization and Angiography," 3rd Ed., Lea and Febiger, Philadelphia, 1986, incorporated herein by reference.

When vascular access is no longer required, the introducer sheath must be removed and bleeding at the puncture site stopped. One common approach to attempt providing hemostasis (the cessation of bleeding) is to apply external force near and upstream from the puncture site, typically by manual or "digital" compression. This approach suffers from a number of disadvantages. It is time-consuming, frequently requiring one-half hour or more of compression before hemostasis is assured. This procedure is uncomfortable for the patient and frequently requires administering analgesics to be tolerable. Moreover, the application of excessive pressure can at times totally occlude the underlying blood vessel, resulting in ischemia and/or thrombosis. Following manual compression the patient is required to remain recumbent for at least six and at times as long as eighteen hours under close observation to assure continued hemostasis. During this time renewed bleeding may occur resulting in bleeding through the tract, hematoma and/or pseudoaneurism formation as well as arteriovenous fistula formation. These complications may require blood transfusion and/or surgical intervention. The incidence of these complications increases when the sheath size is increased and when the patient is anti-coagulated. It is clear that the standard technique for arterial closure can be risky, and is expensive and onerous to the patient. While the risk of such conditions can be reduced by using highly trained individuals, such use is both expensive and inefficient.

To overcome the problems associated with manual compression, the use of bioabsorbable fasteners to stop bleeding has been proposed by several groups. Generally, these approaches rely on the placement of a thrombogenic and bioabsorbable material, such as collagen, at the superficial arterial wall over the puncture site. While potentially effective, this approach suffers from a number of problems. It can be difficult to properly locate the interface of the overlying tissue and the adventitial surface of the blood vessel, and locating the fastener too far from that surface can result in failure to provide hemostasis and subsequent hematoma and/or pseudo aneurism formation. Conversely, if the fastener intrudes into the arterial lumen, intravascular clots and/or collagen pieces with thrombus attached can form and embolize downstream causing vascular occlusion. Also, thrombus formation on the surface of a fastener protruding into the lumen can cause a stenosis which can obstruct normal blood flow. Other possible complications include infection as well as adverse reactions to the collagen implant.

Catheters are also used to treat heart disease which is a major medical ailment wherein arteries become narrowed or blocked with a build-up of atherosclerotic plaque or clot which reduces flow to tissues downstream or "distal" to the blockage. When this flow reduction becomes significant, a patient's quality of life may be significantly reduced. In fact, heart disease patients often die when critical arteries, such as the coronary arteries, become significantly blocked.

However, technology has been developed to open some blocked arteries in the treatment of heart disease. For example, balloon angioplasty has become a well accepted treatment wherein a balloon is inflated within the narrowed vessel to stretch or otherwise deform the blockage into a larger lumen. Alternatively, the blockage can even be removed, such as in a procedure known as atherectomy. In general, these treatments use percutaneous catheters which are inserted into the patients' vessels at a peripheral artery or vein puncture site and guided to the internal blockage site via x-ray visualization. The blockage is then treated remotely by use of hydraulic pressure in the case of balloon angioplasty, or by other actuating means to cause remote cutting or ablation of the blockage in the case of atherectomy.

Coronary Artery Bypass Graft Surgery ("CABG")

In the alternative to using catheters to treat heart disease, or when such catheterizations are contraindicated, some blocked vessels can be treated with coronary artery bypass graft surgery ("CABG"). In conventional CABG techniques, a tubular graft is affixed to a port or aperture in an artery wall distally of the blockage. When the opposite end of the tube is in fluid communication with a pressurized arterial blood supply, such as the aorta, the tubular graft provides a conduit for flow into the vessel lumen distally of the blockage.

Conventional CABG surgery is generally initiated by directly exposing the heart to the surgeon. This is accomplished by opening the patient's chest using known sternotomy and retraction techniques that cut the sternum and spread the rib cage open. Then, one or both lungs are usually deflated and the patient is connected to a respiratory assist machine.

Once the heart is exposed, the patient is connected to a coronary bypass machine so that the blood supply circumvents the heart. In this way, the heart is depressurized so that apertures can be cut into the walls of the vessels for surgical graft attachment. The right atrium (or vena cava) and the aorta each is intubated with cannulas which are connected to an artificial pump and oxygenator. Once these major vessels are cannulated, cardioplegia is delivered to slow or stop the beating motion of the heart. The aorta is then clamped proximally of the aortic bypass cannula, thereby isolating the proximal aortic root from the blood that is being circulated by the bypass machine.

After the heart is isolated from blood pressure, conventional bypass grafting is performed. The required grafts are implanted to feed the coronary arteries distal to the blockage, the clamp is removed from the aorta, the lungs are restored, and the patient is then taken off of the bypass pump.

In one type of CABG method, the bypass grafting is achieved between the aorta and one of the three major coronary arteries or their sub-branches, the left anterior descending artery (LAD), the circumflex artery (CIRC), or the right coronary artery (RCA). In such a case, a saphenous vein is usually taken from the patient's leg and is transplanted as a "homograft" to connect these vessels in the same patient's chest. Artificial grafts have also been disclosed as providing potential utility for this purpose and are herein collectively included in the general discussion of "saphenous veins" as used in CABG procedures.

An alternative CABG method uses the internal mammary artery (IMA) alone or in conjunction with the saphenous vein graft. The IMA is severed at a chosen location and is then connected to an aperture, in a coronary artery.

In either case of using saphenous vein homografts or artificial grafts in CABG surgery, the proximal end of the graft is generally sutured or otherwise is affixed circumferentially to the tissue surrounding an aperture that is punched into the wall of the aorta. In this arrangement, the lumen of the graft communicates with the vessel through the aperture, wherein ideally the aperture approximates the inner diameter of the graft lumen. The opposite, distal end of the graft is sutured to an aperture formed in the wall of the coronary vessel distal to the blockage.

The fluid connections between a graft and a vessel are herein referred to as "anastomoses." In the instance of CABG, "proximal anastomoses" and "distal anastomoses" are terms used when referring to grafting to the aorta and the coronary artery, respectively. In most CABG procedures using saphenous vein grafts, the distal anastomosis is performed first, followed by the proximal anastomosis.

For the CABG method using the IMA, only one distal anastomosis is formed distal to the arterial blockage. A proximal anastomosis to the aorta is not required as it is in a saphenous vein graft procedure because the IMA's natural arterial blood flow feeds the heart.

In conventional CABG surgery methods such as those just summarized, the timing and technique of the anastomosis procedures are critical factors to procedural success. In fact, it is believed that three critical determinants which affect outcomes of CABG surgery are: (1) time the patient spends on bypass, (2) time the patient spends with a clamped aorta, and (3) the quality of the anastomoses. It is generally believed that a CABG patient's operative and peri-operative morbidity are directly related to how long the patient must be on heart bypass. In fact, it is generally understood that the risk of patient morbidity is believed to rise significantly after a threshold time of one hour on bypass. Perhaps the most prevalent complication arising from prolonged cardiac bypass is the high risk of distal thrombus created by the artificial plumbing. For example, such thrombi can embolize into the neurovasculature and potentially can cause a stroke. In analyzing the timing of individual CABG steps against the backdrop of a patient's critical time on bypass, the time spent anastomosing the grafts to vessels emerges as a controlling factor. The average time for suturing one anastomosis is approximately 7–10 minutes. Furthermore, it is believed that an average CABG procedure involves approximately five anastomoses: two saphenous vein grafts, each with a proximal and a distal anastomosis, and one internal mammary artery having only one distal anastomosis. Therefore, the average time for graft suturing ranges from 35 minutes to 50 minutes—in any case a significant portion of the 60 minute critical threshold to patient morbidity. Closely related to the time spent on bypass is a second CABG success factor related to the extent and time of aortic cross-clamping. It is believed that the inherent crushing force from a cross-clamp across the bridge of the muscular aortic arch may be associated with a high degree of tissue trauma and structural damage. Additionally, hemostasis formed at or adjacent to the cross clamp, perhaps in conjunction with the tissue trauma of clamping, may also be a source of unwanted thrombogenesis.

In addition to the timing of anastomosing grafts and extent and duration of aortic cross-clamping, the quality of interface between the graft and vessel is also believed to be an indicator of procedural success. The accuracy, trauma, and repeatability of suturing, as well as the three-dimensional interface formed between the conduits at the anastomosis site, are significant variables in conventional manual surgical techniques. These variables are believed to significantly affect the short or long-term success of conventional CABG anastomosis procedures.

Limitations of Conventional CABG Devices & Methods

Both of the critical CABG success indicators summarized above—time on cardiac bypass and quality of anastomosis suturing—are directly affected by inherent limitations in the devices used in conventional CABG procedures. It is believed that improvements to these devices and related methods of use may provide for more rapid and reliable vessel-graft anastomosing. For example, conventional "surgical punches" are devices that cut or "punch" a plug in vessel wall tissue to form an aperture in the wall. In a CABG procedure, the tissue surrounding a punched-out aperture provides the substrate upon which a graft may be sutured to form an anastomosis. One procedural limitation in using conventional surgical punches is that hemostasis can not be maintained at a vessel wall after a plug of tissue is punched out and removed. Therefore, an aperture in an aortic wall during a saphenous vein graft procedure can only be made when that portion of the aorta is cross-clamped, bypassed, and depressurized. Otherwise, the high blood pressure and flow in the aorta would cause significant bleeding during the period from punching the aperture to forming the anastomosis. Because of this limitation in conventional surgical punches, the threshold 60 minute coronary bypass clock begins running before punching the aorta.

The prior art fails to disclose or fulfill the need which exists in the field of medical devices and methods for: suturing tissue by proximally drawing sutures through a tissue layer in the proximity of an aperture; suturing vascular tissue while maintaining adequate perfusion or hemostasis, or both; a medical device assembly or surgical method that allows for a graft to be anastomosed to an aperture in a vessel wall while maintaining hemostasis at the anastomosis with physiological flow and/or pressure in the vessel lumen; a surgical punch assembly that punches and removes tissue to form an aperture in a vessel wall while maintaining hemostasis at the aperture with physiological flow and/or pressure in the vessel lumen; a cannula that includes a tube and a hemostatic valve that slideably receives an elongated medical device which is radially removable from the tube and hemostatic valve; a medical device assembly that automatically and repeatably places suture thread through vessel wall tissue surrounding an aperture in the vessel wall in a suture pattern that is useful for anastomosing a tubular graft to the aperture; and a medical device assembly that deploys a suture with one end extending through the tissue that surrounds a punched aperture in a vessel wall and the opposite suture end extending radially through a tubular graft wall adjacent an open end of the graft, such that a vessel anastomosis may be rapidly and repeatably performed in a CABG procedure even while the vessel is under physiological flow.

SUMMARY OF THE INVENTION

The present invention provides a device for suturing tissue in the proximity of an aperture in a tissue layer. The device includes a shaft having a proximal and distal end. The shaft is adapted for advancing through the aperture. At least one needle is carried near the distal end of the shaft. A length of suture is secured to the needle. The device includes means for drawing the suture through the tissue in the proximity of the aperture. The device also includes means for maintaining adequate perfusion through the vessel while advancing the distal end of the shaft through the aperture in the tissue layer, drawing the suture through the tissue and securing the suture to the tissue in the proximity of the aperture. The maintaining means and drawing means are integrally formed with the shaft.

Another device for suturing tissue in the proximity of an aperture in a tissue layer is provided by the present invention. The device includes a shaft having a proximal and distal end. The shaft is adapted for advancing through the aperture. At least one pair of needles is carried near the distal end of the shaft. A length of suture is secured to and extends between the pair of needles. The device includes means for drawing the pair of needles proximally through the tissue in the proximity of the aperture. The drawing means is integrally formed with the shaft.

A device for suturing vascular tissue in the proximity of an aperture in a vessel wall is also provided. The device includes a shaft having a proximal and distal end. The shaft is adapted for advancing through the aperture and at least one needle is carried near the distal end of the shaft. A length of suture is secured to the needle. Means for drawing the suture through the vascular tissue in the proximity of the aperture is included. Integrally formed with the shaft is means for maintaining adequate perfusion or hemostasis, or both, while advancing the distal end of the shaft through the aperture in the vessel wall, drawing the suture through the vascular tissue and securing the suture to the vascular tissue in the proximity of the aperture.

The present invention also provides a device for suturing the wall of a tubular graft. The device includes a shaft having a needle carrying portion adapted to be positioned coaxially within the wall of the tubular graft. A needle is secured to and extendible from the needle carrying portion. A suture is secured to the needle. An actuator is provided for extending the needle outwardly from the shaft and through the wall of the tubular graft.

Another aspect of the present invention includes graft anastomosis assembly for suturing a tubular graft about an aperture in the wall of a vessel. The assembly includes a vessel suturing device having a vessel shaft with a vessel needle carrying portion and a vessel needle secured to and extending outwardly from the vessel needle carrying portion. A graft suturing device has a graft shaft with a graft needle carrying portion and a graft needle secured to and extending outwardly from the graft needle carrying portion. A suture with a first suture portion is secured to the vessel needle and a second suture portion is secured to the graft needle. The vessel suturing device is adapted to place the first suture portion proximally from the interior of the vessel and through the vessel wall tissue adjacent the aperture. The graft suturing device is adapted to place the second suture portion proximally from the interior of the graft and through a wall of the graft, such that the first and second suture portions form a loop which is tightened to secure a portion of the graft to the vessel.

A graft assembly for anastomosing a tubular graft and vessel is also provided by the present invention. The tubular graft has a graft wall that forms a graft lumen with an open end. The graft wall has suture ports circumferentially spaced in a predetermined pattern near the open end. The assembly includes sutures in the predetermined pattern. Each suture has a first suture portion extending through one of the suture ports in the graft wall. Each suture has a second suture portion extending along at least a portion of the graft lumen.

Another aspect of the present invention provides a surgical punch assembly for making an aperture in a tissue wall. The assembly includes a surgical punch which has a tubular sleeve with a distal end defining a sleeve lumen with an inner diameter. The punch has an actuating member extending distally through the sleeve. The actuating member has a distal portion with a disk secured thereon. The disk has a outer diameter larger than the actuating member and is adapted to the distal end of the sleeve, whereby tissue captured between the disk and sleeve is cut to form the aperture when the disk is proximally drawn to engage the distal end of the sleeve. The punch includes an actuator on a proximal end of the surgical punch that is engaged with the sleeve and also with the actuating member. The actuator is adapted to actuate longitudinal movement of the disk relative to the sleeve. The punch also includes a cannula having a cannula lumen and a hemostatic valve that forms an inner valve bore. The hemostatic valve is located within the interior of the cannula lumen. The cannula lumen and inner valve bore are coaxially slideable over the surgical punch, whereby the cannula can be advanced over the surgical punch and into the aperture which is cut in the tissue wall and that the punch can be removed proximally through the cannula to remove a plug of tissue from the aperture while maintaining hemostasis.

The present invention also provides a medical catheter assembly which includes a body having a length with a catheter lumen extending longitudinally along the length. The body includes an elongate tube having a tubular wall that defines a tube lumen which defines at least a portion of the catheter lumen. The tubular wall has a tube seam along a longitudinal axis thereof that is circumferentially severable. The assembly also includes a hemostatic valve located within the interior of the catheter lumen and has a circumferential wall formiing an inner valve bore which is adapted to slidably receive an elongate medical device therethrough. The circumferential wall has a valve seam that is circumferentially severable, whereby hemostasis is maintained about an elongate medical device disposed within the tube lumen and inner valve bore. The medical catheter assembly is radially removable from the elongate medical device by circumferentially separating the tube seam and the valve seam.

A further aspect of the present invention includes a method of suturing vascular tissue in the proximity of an aperture in the wall of a vessel. The method includes maintaining adequate perfusion of blood through the vessel or hemostasis, or both, while advancing a suture device through an aperture in the vessel and suturing the vascular tissue in the proximity of the aperture.

Another aspect of the present invention is a method for suturing tissue in the proximity of an aperture in a tissue layer. The method includes passing at least one end of a suture from the interior of the vessel proximally through a suture port or penetration site in the tissue in the proximity of the aperture and forming a loop with the other end of the suture to secure the suture.

Another aspect of the present invention includes a method of performing a coronary artery bypass graft surgery. The method includes anastomosing a graft tissue to an aperture in a vessel wall while maintaining adequate perfusion or hemostasis, or both, in the proximity of the aperture.

Another method of performing coronary bypass surgery includes maintaining the heart under pressure and maintaining adequate perfusion through the proximal or distal arteries while advancing a suture device through the aperture in the vessel wall, suturing the vascular tissue in the proximity of the aperture, and removing the suture device from the vessel while drawing the vascular tissue in the proximity of the aperture in apposition to the graft.

The present invention also provides a method for anastomosing graft-to-vessel tissue. The method includes: forming an aperture having an aperture diameter in a vessel wall; bringing an open end of a tubular graft into contact with the vessel wall tissue adjacent the aperture such that a lumen of the graft communicates with the aperture and has an inner diameter that approximates the aperture diameter; and, securing the open end of the tubular graft to the vessel wall tissue surrounding the aperture, wherein the method is performed while maintaining hemostasis.

BRIEF DESCRIPTION OF THE DRAWINGS

In the drawings, which comprise a portion of this disclosure but are not to scale:

FIG. 3 is a cross-sectional view of the device of FIGS. 2A and 2B, taken along line 3—3 of FIG. 2B;

FIG. 8 illustrates the X-pattern of the tied suture applied by the suturing device;

FIG. 9A is an elevational view of a surgical punch assembly for hemostatically forming an aperture in a vessel, such as the aorta;

FIG. 9B is an enlarged partially sectional view of the distal end portion of the surgical punch of FIG. 9A;

FIG. 10A is an enlarged elevational view showing a dilating tip of the surgical punch of FIG. 9A;

FIG. 10B is an enlarged elevational view showing a sharpened blade on the dilating tip of FIG. 10A;

FIGS. 13 and 14 are views similar to FIGS. 9A–B showing the operation of the surgical push assembly of FIGS. 9A–B wherein the hemostatic cannula is placed over the surgical punch, through the aperture in the vessel wall, and into the vessel lumen;

FIG. 15 is a partial view of the device of FIGS. 9A–B showing the surgical punch being withdrawn from the hemostatic cannula;

FIG. 16 is a view of the hemostatic cannula being radially removed from an anastomosis suturing device after the distal end portion of the anastomosis suturing device has been inserted into the vessel through the hemostatic cannula;

FIG. 17A is an elevational view of the hemostatic valve of the hemostatic cannula;

FIG. 17B is an elevational view of the hemostatic valve of FIG. 17A with a valve seam that is circumferentially separated;

FIG. 18A is an elevational view of the housing of the hemostatic cannula;

FIG. 18B is an elevational view of the housing of the hemostatic cannula with a housing seam that is circumferentially separated;

FIG. 24A is an enlarged sectional view of the distal end portion of the anastomosis suturing device which is used to dispose sutures through the wall of the vessel;

FIG. 24B is a cross-sectional view taken along line 24B—24B of FIG. 24A;

FIG. 24C is a cross-sectional view taken along line 24C—24C of FIG. 24A;

FIG. 25 is a view of the distal tip of the suturing device showing the external configuration thereof;

FIG. 26 is sectional view of a proximal portion of the anastomosis suturing device which includes a graft suturing device used to dispose sutures through the wall of the vessel graft;

FIG. 27 is a cross-sectional view taken along line 27—27 of FIG. 25; and

FIGS. 28A–C are cross-sectional views taken along line 28—28 of FIG. 25 showing the needles of the proximal, portion retracted, partly extended, and fully extended, respectively.

DETAILED DESCRIPTION OF THE INVENTION

As used herein, the term "distal" is generally defined as in the direction of the patient, or away from a user of a device, or in a downstream direction relative to a forward flow of blood. In the context of a medical device intervention with or through a vessel wall, "distal" herein refers to the interior or the lumen side of the vessel wall.

Conversely, "proximal" generally means away from the patient, or toward the user, or in an upstream direction relative to a forward flow of blood. In the context of a medical device intervention with or through a vessel wall, "proximal" herein refers to the exterior or outer side of the vessel wall.

Additionally, "oblong" is herein intended to mean oval, elliptical, or otherwise having a generally rounded shape that is not perfectly circular. In particular, the term describes the shape of a tubular graft end cut at an acute angle relative to the plane perpendicular to the tissue walls defining the graft.

The term "hemostasis" is herein used to mean the arrest of bleeding or substantially blocking flow of blood outwardly from a vessel lumen while the vessel lumen is pressurized or sustaining physiological blood flow. This amount of blockage or occlusion to flow is further defined such that the blood loss which is experienced is less than an amount which would affect procedural methods or outcomes according to a physician user of a device of ordinary skill in the art. In other words, "hemostasis" is not intended to mean only "total hemostasis" such that there is a total lack of blood loss. Rather, the term is used to also mean "procedural hemostasis" as a relative term in its use among physicians of ordinary skill.

Similarly, "occlusion," "occlude," "blockage," "block . . . plugging", "block," or variations thereof are all terms which are herein intended to have a procedurally relevant definition in the context of their use. For instance, an aperture is "occluded" although there is some measurable flow therethrough, but that flow is so low such that the intended procedural benefit of occlusion is at least partially achieved. Certainly, such terms also properly include within their scope a "total effect" definition, as well.

The term "perfusion" is herein used to mean the flow of blood or other unit of perfusate (the fluid used for perfusion) per unit volume of tissue. Physiological perfusion refers to the amount of blood flow present when the body is functioning normally. For example, physiological perfusion usually prevents clinically significant ST elevations which is one of the most sensitive indicators of inadequate perfusion. Adequate perfusion refers to the amount of blood flow that avoids the clinical requirement of transfusing the patient or that is needed to prevent tissue necrosis distal to the aperture in the blood vessel.

Figure 1:
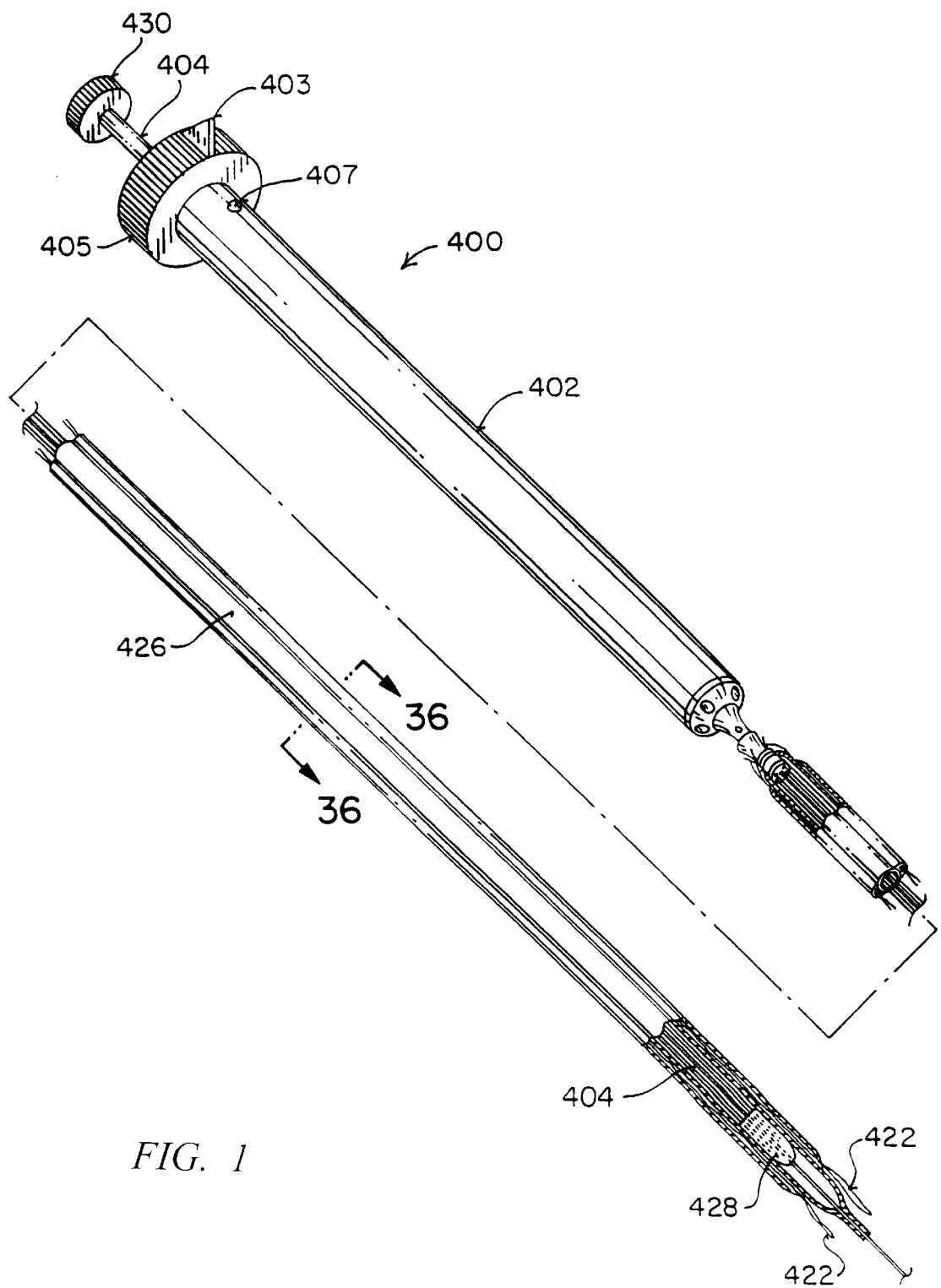
FIG. 1 is a perspective view of an embodiment of a suturing device constructed in accordance with the principles of the present invention.

Referring to FIGS. 1–3, a suture applying device 400 which is suitable for suturing and sealing of percutaneous vascular puncture site, particularly those made to the femoral artery in a patient's groin, will be described. It will be appreciated, however, that the device of the present invention can be readily adapted for use with punctures made to other hollow body organs and lumens, although it may be necessary to modify the dimensions and other particular aspects of the device to accommodate the different usage environment.

Figure 2A:
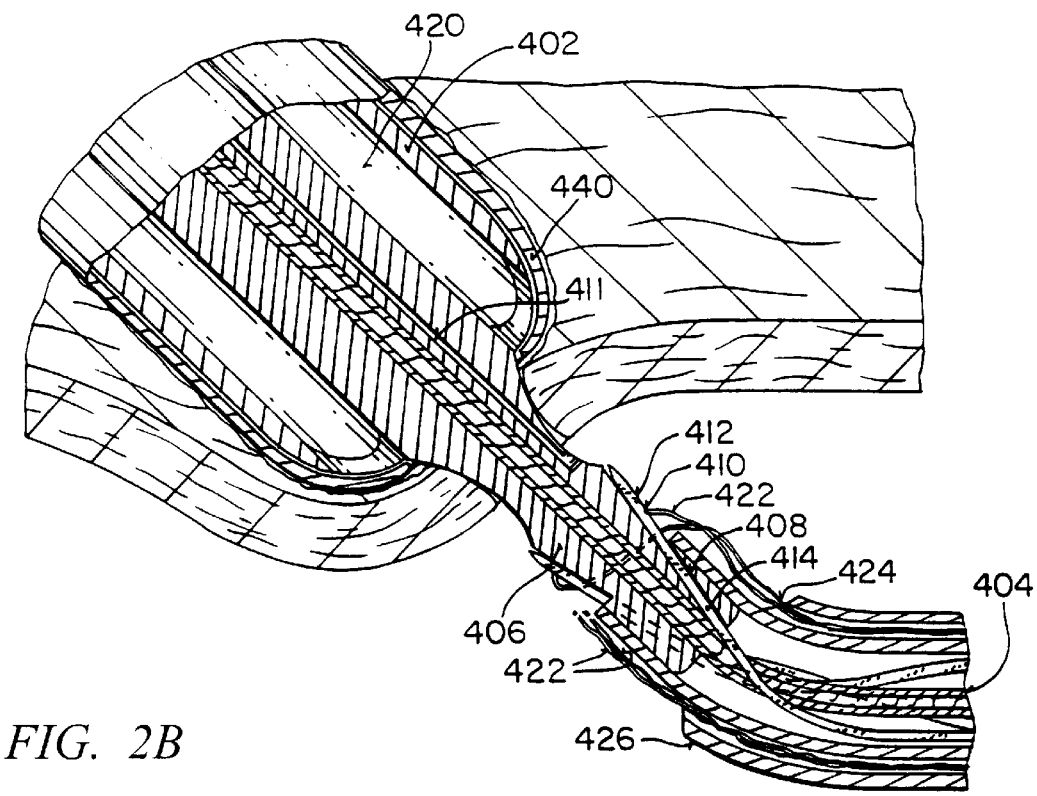
FIG. 2A is a detail view of the distal end of the guide body of the suturing device of FIG. 1, shown with the needles retracted fully within the guide body.
Figure 2B:
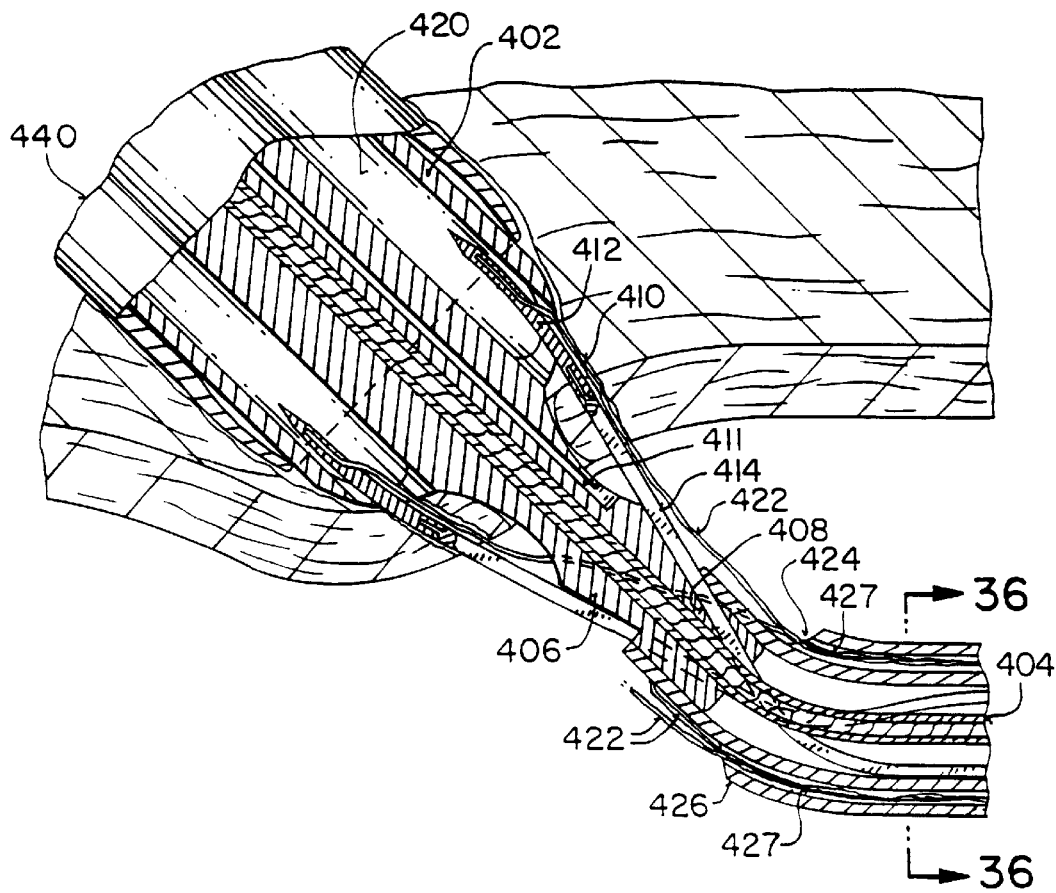
FIG. 2B is a view similar to FIG. 2A, except that the needles have been partially drawn back into the guide body.

The device 400 comprises a guide body 402 and a needle shaft 404. The guide body 402 includes a guide tip 406 at its distal end, which guide tip includes a plurality of guide channels 408 which receive the proximal ends of needles 410. An aligning arrow 403 is mounted on handle 405 located at the proximal end of the guide body 402. A marker lumen bubble 407 is located below the aligning arrow and serves to indicate when the distal end of the guide body has entered a blood vessel, as described in the embodiment below. An indicator lumen 411 which permits the flow of blood to the marker lumen bubble 407 is illustrated in FIGS. 2A and 2B.

The needles 410 as illustrated comprise a sharpened tip section 412 and an elongate shank portion 414, but may also be manufactured as an integral piece. The shank portion 414 will be sufficiently long so that the needles may be pushed from their butt end by a support holster 428 fixedly attached to the needle shaft 404 in order to advance the needles through the tissue to be sutured and fully through the guide body 402 inserted together with support sheath 440 in the associated tract so that no capture mechanism will be required.

The guide body 402 further includes a plurality of needle lumens 420 which are axially aligned and spaced about the periphery of the guide body. As best seen in FIG. 2B, the needles 410 will enter the distal ends of the lumens 420 as the needles are advanced proximally relative to the guide body.

A flexible needle sheath 426 will be attached to the guide tip 406 of guide body 402. The central lumen of the needle sheath 426 receives a support holster 428 attached to the distal end of the needle shaft 404, as well as the needles 410. As with previous embodiments, the butts of the needles 410 are removably received within the support holster 428. The sheath 426 will be sufficiently long to permit the needles to extend at least 5 cm beyond the distal end of guide body 402.

Prior to use, the suture applying device 400 will be in the configuration illustrated in FIGS. 1 and 2A. That is, the needle shaft 404 will be distally positioned within the guide body 402 and needle sheath 426. In particular, the tips of needles 412 will lie just at the guide tip 406 so that they may be easily advanced through the arterial tissue surrounding the arteriotomy. That is, the tips of the needles will be generally retracted within the guide tip 406. A length of suture 422 is attached to the proximal tips 412 of opposed pairs of needles 410, with the connecting suture being stored in side lumens 427 extending axially along the exterior of the needle sheath 426. As best observed in FIGS. 2A and 2B, the suture 422 extending between one pair of opposed needles is received in a first of the side lumens 427, while the suture extending between the other pair of opposed needles is received in the second of the side lumens. While it would be possible to store the suture 422 in the lumens 420 of the guide body 402 (and thus eliminate the need for side lumens 427), such storage is less preferred since it increases the risk that the suture will become entangled with the needles 410 as they are withdrawn proximally. The use of side lumens 427 greatly simplifies feeding of the suture as the needles 410 are withdrawn.

After the guide tip 406 has been past through the puncture site to be sutured, the needles may then be drawn proximally forward through the tissue to be sutured by drawing proximally on handle 430 at the proximal end of needle shaft 404. The method of the present invention will now be described in more detail with reference to FIGS. 4–7.

Figure 4:
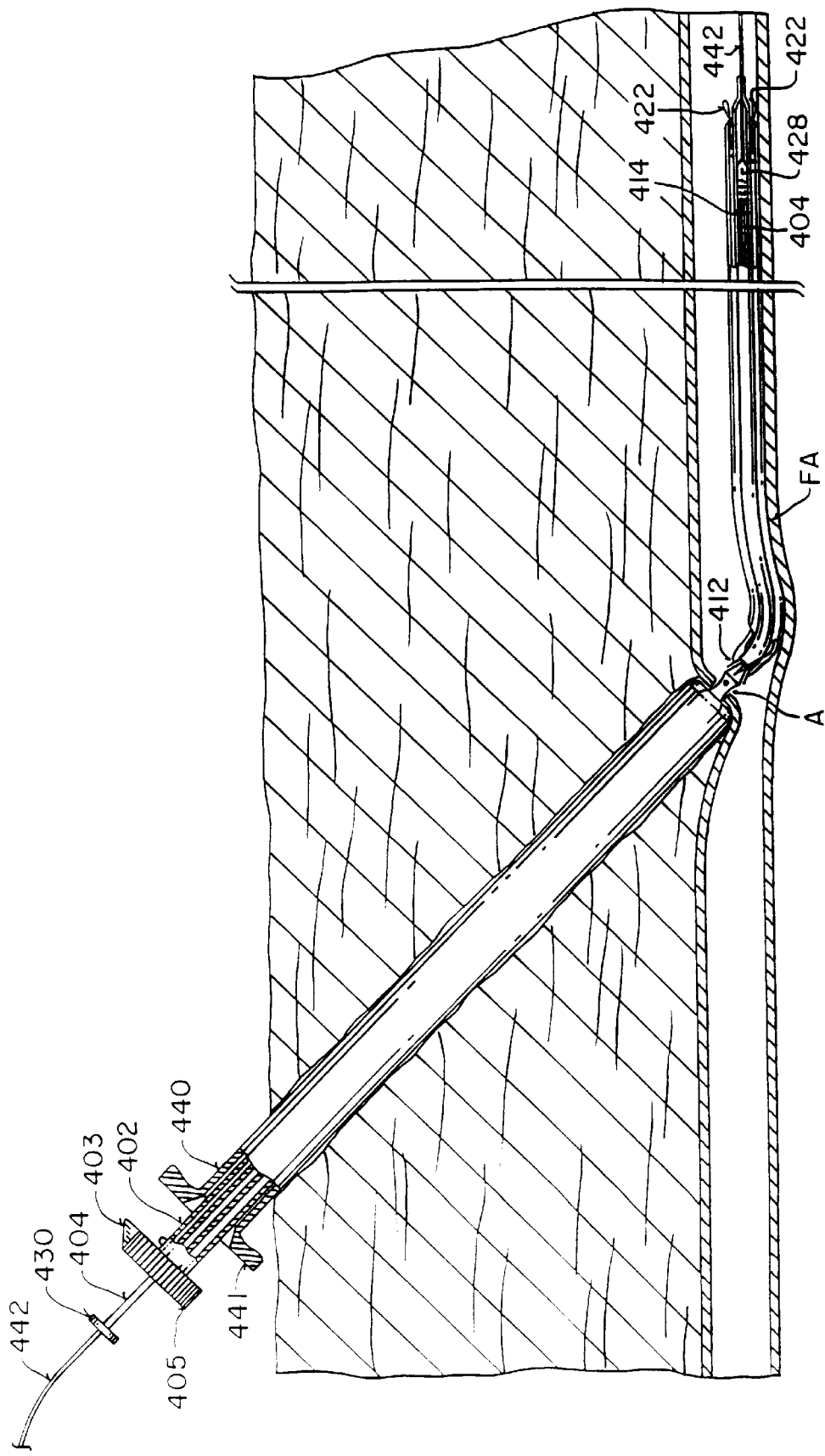
FIGS. 4–7 illustrate the method of the present invention using the suturing device of FIG. 1.

The situation following an interventional or other vascular procedure, where the attending physician is satisfied that the puncture site may be sealed, is illustrated in FIG. 4. A conventional introducer sheath is in place with a guidewire passing into the femoral artery. The conventional introducer sheath is withdrawn after assuring that an appropriate guidewire for the suturing process is in place. The device 400 (including a support sheath 440 which initially covers the ports to the needle lumens 420) will then be introduced over the guidewire, as illustrated in FIG. 4. The needles 410 and sutures 422 mostly encased by flexible needle sheath 426, will be fully advanced into the femoral artery FA past the arterial puncture site A. Handle 441 on support sheath 440 is then partially withdrawn proximally to expose the needle lumens 420 (as shown in FIGS. 2A, 2B, and 5).

Figure 5:
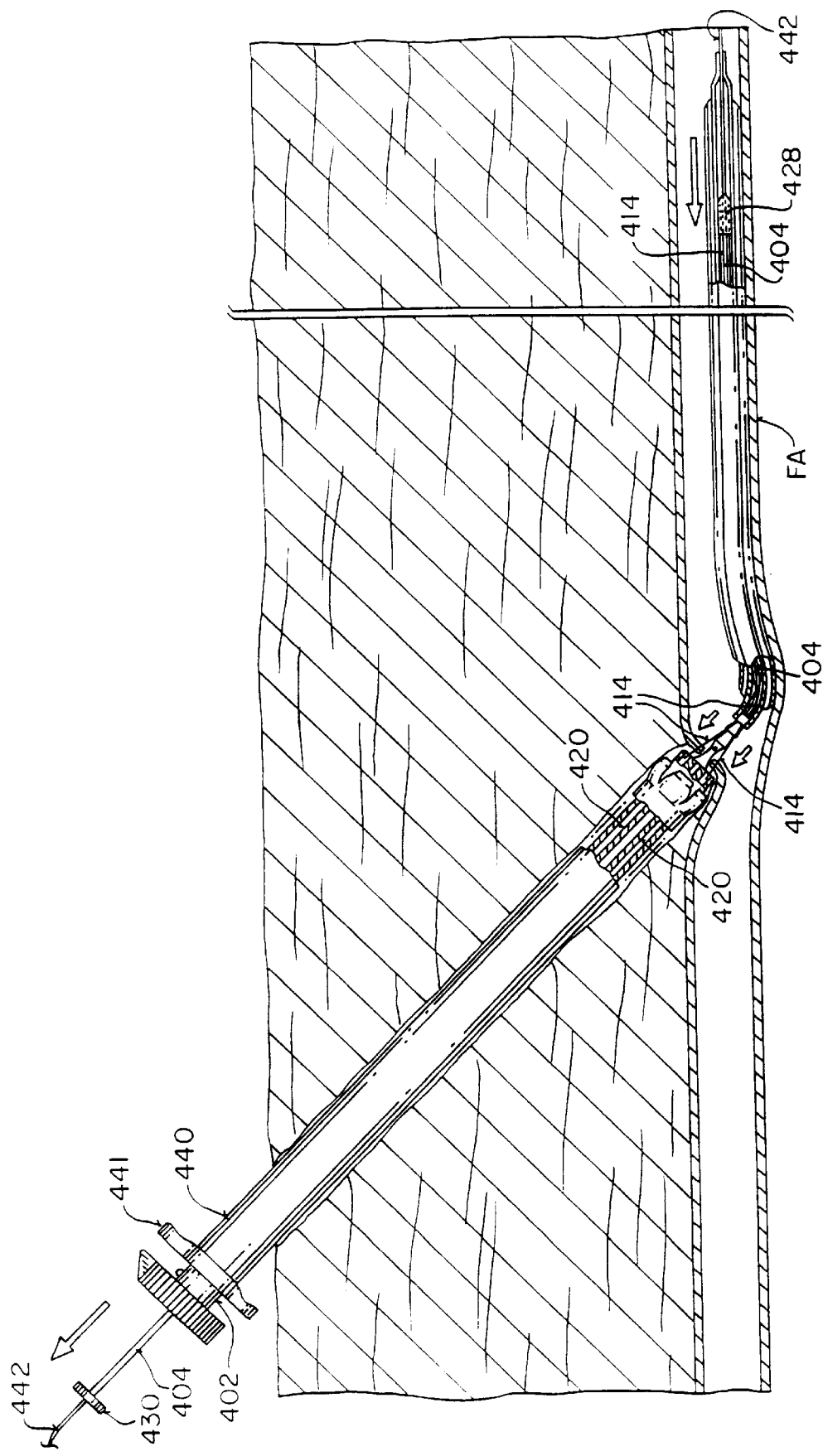
Figure 7:
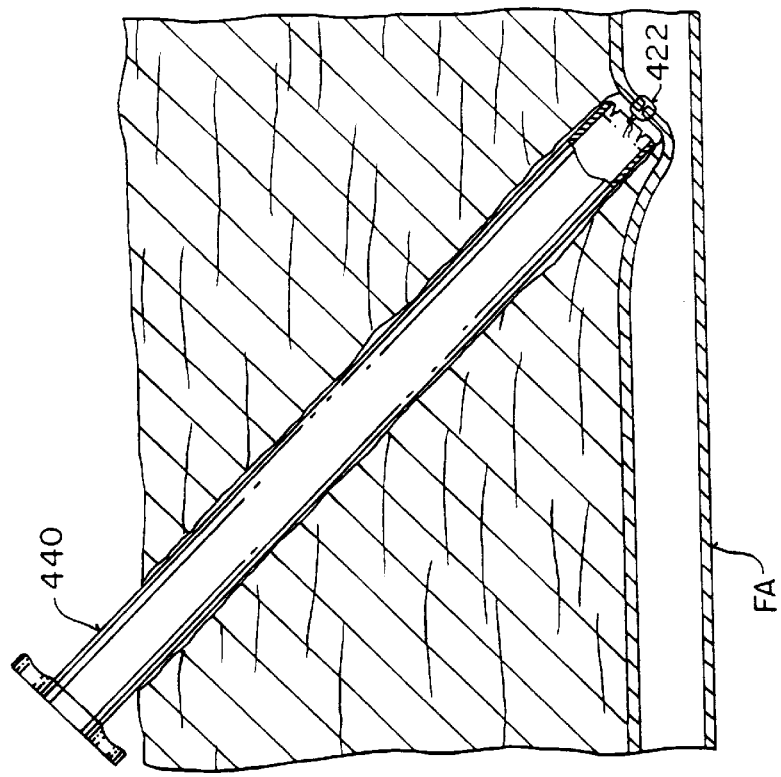
Figure 6:
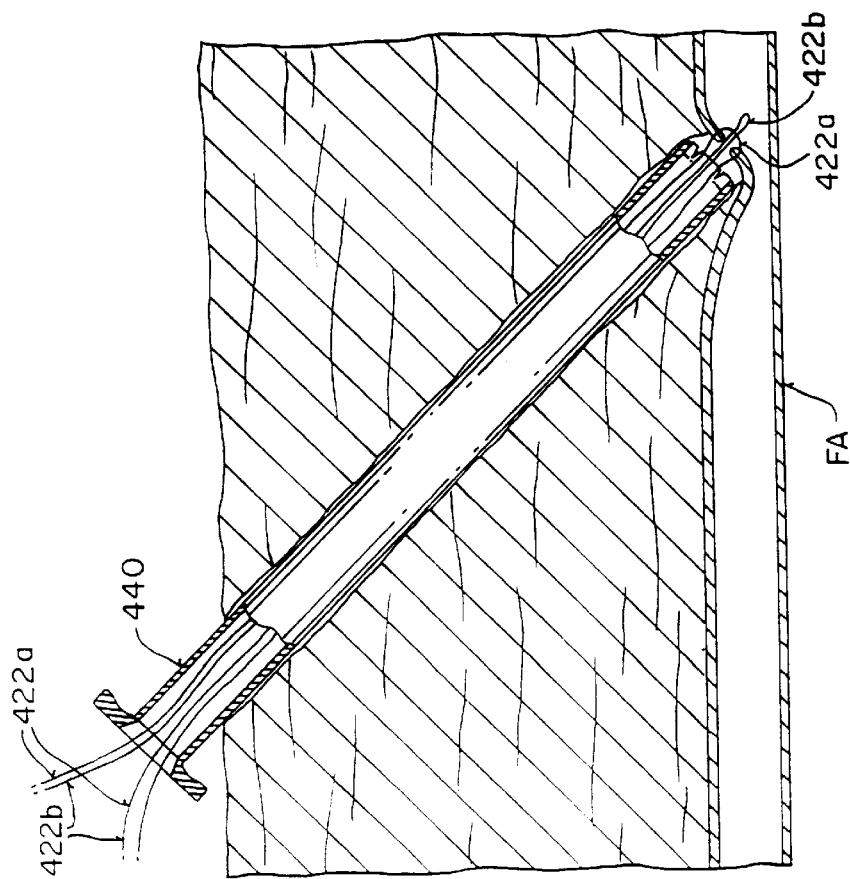

Handle 430 will then be drawn proximally outward relative to the guide body 402, causing the needles 410 to pass through the superficial wall of the femoral artery FA and into the needle lumens 420, as illustrated in FIGS. 2B and 5. The handle 430 may continue to be drawn proximally (i.e., outward from the patient) in order to continue to pull the needle shaft 404 through the guide body 402. Such movement of the needle shaft 404, in turn, continues to draw the needles 410 outward through the lumens 420 of the guide body 402 until the tips of the needles are exposed. The user may then grasp the needles and continue to draw them out until the suture is available to the user. The guide body 402 may then be withdrawn from the support sheath 440, leaving a portion of the needle sheath 426 still in the puncture site A to maintain hemostasis. The suture can then be tied and the knot pushed back down through the support sheath 440. The knot will then only be tightened when the needle sheath is finally withdrawn from the puncture site A.

It can be seen that the guide tip 406 deflects the needles radially outward so that the pattern of four needles engages the artery wall in an approximately square pattern about the arteriotomy A. After the sutures are tied and the knots advanced back through the support sheath 440, the resulting pattern of tied suture will appear as in FIG. 8 when viewed towards adventitial surface of the femoral artery FA surrounding the arteriotomy A.

Device 400 has certain advantages over the previous embodiments. Since it is not necessary to capture the needles using an internal capture mechanism, the needles need not have barbs. Such barbless needles will minimize trauma to the arterial tissue around the puncture site A and simplify the procedure. The guide body 402 and guide tip 406 are designed as an integral structure to assure that needles 410 will be precisely centered around the puncture site A, and will very reliably enter the needle lumens 420 in guide body 402. Also, tip 406 will occlude the arteriotomy puncture during the performance of the procedure, providing hemostasis. Moreover, the entire procedure is simplified, with fewer discrete steps being performed. The user need only introduce the device over-the-wire and thereafter draw out the needle shaft to carry the needles through the tissue to be sutured and outward through the guide body, where the suture becomes accessible and may be tied in a conventional manner.

The present invention also provides several devices which comprise a graft anastomosis assembly. One of the preferred embodiments of the graft anastomosis assembly and component devices depicted in the drawings is used to form an aperture or hole in a tissue wall, such as the wall of an aorta or other vascular tissue. Then the assembly sutures a graft to the tissue wall at the site of the aperture. Preferably, hemostasis is maintained during the entire procedure. Furthermore, the graft anastomosis assembly and devices can maintain perfusion beyond the area of the device introduction through the vascular tissue.

One embodiment of a first device, is a surgical punch assembly 10 that includes a surgical punch 12 and a cannula 14 as shown in FIGS. 9–14. Referring specifically to FIGS. 9A–9B, the surgical punch 12 includes a dilating tip 16 attached at its proximal end to a shaft 18, a hollow sleeve 20 having a distal end 22 that includes an integrally formed cutting blade 24, and an actuating mechanism 26 that includes a hand grip 28 for operating surgical punch 12. The cannula 14 is positioned coaxially about the hollow sleeve 20 and the shaft 18, and is described in further detail in reference to FIGS. 16, 17A–B, and 18A–B.

As depicted in FIGS. 9A and 9B, the dilating tip 16 has been pushed through a vessel wall 30. The distal end 32 of the dilating tip has a tapered, conical shape that forms and dilates a puncture site 34 in the vessel wall. The dilating tip 16 also includes a proximal cylindrical section that forms a disk 36 to which the shaft 18 is attached. Preferably, the outer diameter of disk 36 is slightly smaller than the inner diameter of the hollow sleeve 20 so that the dilating tip 16 may be at least partially withdrawn telescopically into the hollow sleeve 20 by sliding the proximal cylindrical section of the disk 36 within the interior of the hollow sleeve 20. As the dilating tip 16 passes through the vessel wall 30, the dilated tissue around the puncture site 24 responds elastically and compresses onto the shaft 18, thereby maintaining hemostasis. In this position, the distal end 22 of the hollow sleeve lies adjacent the proximal side of the vessel wall 30.

FIGS. 10A and 10B illustrate two preferred embodiments of the dilating tip 16. In FIG. 10A, a first embodiment of the dilating tip 16A has a distal end 32A with a distal tip 38 having a rounded shape to provide for an atraumatic entry through the vessel wall 30. The distal tip 38 allows for increased safety against traumatizing the vessel wall intima opposite the puncture site 34 upon advancing the dilating tip 16 into the vessel lumen 40.

In FIG. 10B, a second embodiment of the dilating tip 16B has a distal end 32B with a distal tip 42 having a puncture blade to provide for the initiation of a procedure such as an anastomosis by puncturing the vessel wall 30 under hemostasis. Pressing the puncturing blade of the distal tip 42 against the vessel wall 30 and continuing to advance the dilating tip 16B through the puncture site 34, provides instant sealing of the dilated tissue of the puncture site hemostatically.

Figure 11:
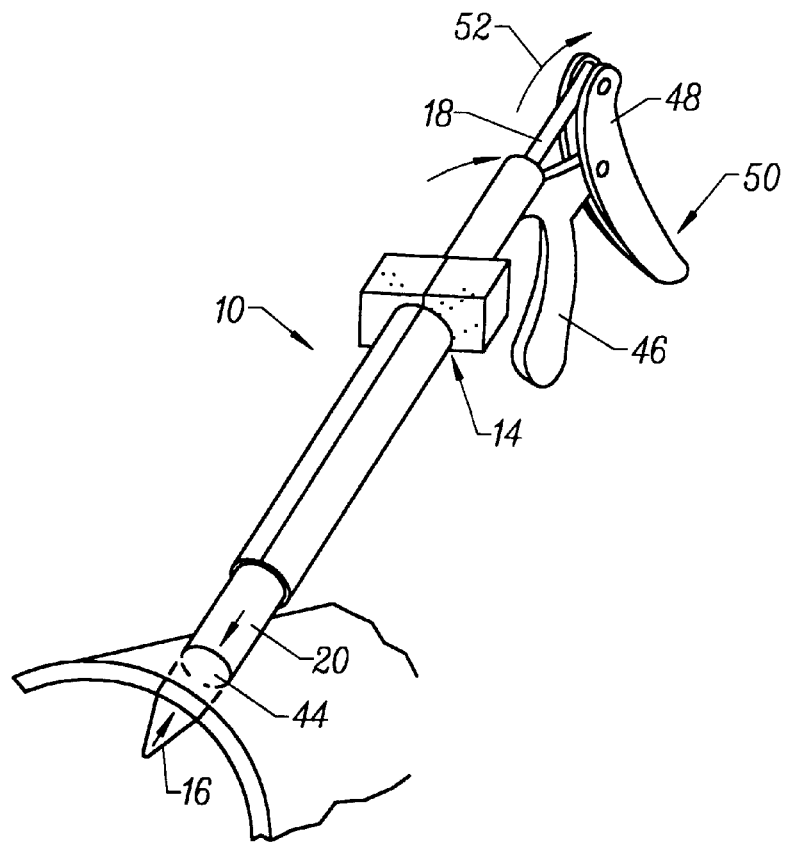
FIGS. 11 and 12 are views similar to FIGS. 9A–B showing the operation of the surgical punch to excise tissue from the wall of the vessel to form the aperture.
Figure 12:
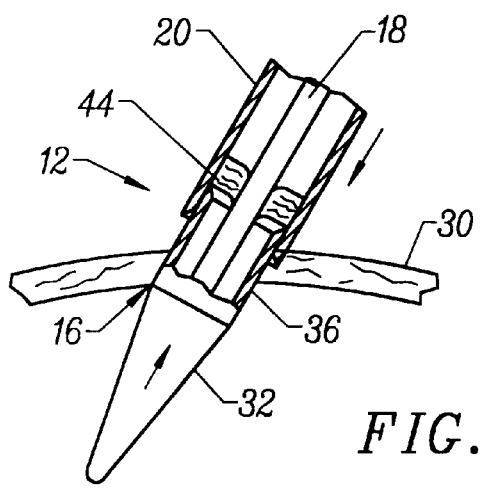

In FIGS. 11 and 12, a plug 44 of tissue from the vessel wall 30 is excised and an aperture is hemostatically formed in the vessel wall through actuation of the surgical punch 12 via the actuating mechanism 26. The hand grip 28 includes of a distal member 46 that is attached to the hollow sleeve 20 and proximal lever member 48 that is pivotally attached to the distal member 46 and the proximal end of shaft 18 to form the actuating mechanism 26. When the two members 46 and 48 are squeezed together (depicted schematically by arrow 50 in FIG. 11) the hollow sleeve 20 is advanced distally as indicated by arrow 52 and the dilating tip 16 is moved in a proximal direction until it telescopically engages the hollow sleeve 20. The telescopic engagement between the outer diameter of disk 36 and the inner diameter of the hollow sleeve 20 causes the plug 44 of tissue to be sheared by the cutting blade 24 at the distal end 22 of the hollow sleeve and pushed proximally into the interior of the sleeve 33 as the disk 25 further telescopes within the interior of the hollow sleeve 20. As a result, the plug 44 of tissue is prevented from occluding the vessel in any way. Preferably, the plug 44 of tissue has an oblong shape so that the aperture formed thereby may be anastomosed to an oblong end of a tubular graft that is cut at an oblique angle.

Although one embodiment of the cutting blade 24 and the actuating mechanism 26 is illustrated, alternative embodiments are suitable for use with the present invention as may be apparent to one of ordinary skill in the art. For example, and not limitation, the dilating tip 16 can alternatively include a distal cutting blade 54 at the proximal end of the disk 36. The distal cutting blade 54 engages the interior of the vessel wall 30 to cut the plug 44 of tissue as it telescopically engages the distal end 32 of the hollow sleeve. The distal cutting blade 54 can be used either alone, or in combination with, the cutting blade 24 at the distal end 22 of the hollow sleeve, as is shown in FIG. 9B. A variety of suitable punch/cutting devices, such as circular blades, anvils, and the like, as well as actuating mechanisms, are disclosed in the following prior documents which are hereby incorporated in their entirety by reference thereto: U.S. Pat. Nos. 3,104,666; 3,776,237; 4,018,228; 4,216,776; and 5,192,294 and U.S. Des. Pat. No. 372,310.

As shown in FIGS. 13 and 14, the cannula 14 is slidably received about the hollow sleeve 20. After creating the puncture site 34 in the vessel wall 30, the cannula 14 is advanced so that the distal end 56 of the cannula extends through the puncture site and into the lumen 40 of the vessel. Once distal end 56 of the cannula extends into the vessel lumen 40, the dilating tip 16 and hollow sleeve 20 are withdrawn proximally from the cannula 14 as shown in FIG. 15.

The cannula 14 is shown in detail in FIGS. 14 and 15. The cannula 14 is shown to include a tube 58, a hemostatic valve 60, and a housing 62. The tube 58 is partially defined by the distal end 56 of the cannula, which preferably has a tapered shape. A tube seam 64 extends longitudinally along the length of the tube 58 and is circumferentially severable. The tube seam 64 is formed by two opposing wall portions 66, 68. The tube seam 64 allows the cannula 14 to be radially removed from coaxial engagement within the tube 58 and within a valve bore of the hemostatic valve 60.

A preferred embodiment of cannula 14 is shown in FIGS. 15 and 16. The tube 58 of cannula 14 is formed by two radially symmetrical segments 70 and 72 that are joined at a pair of circumferentially severable tube seams 64, 74. The housing 62 includes the hemostatic valve 60 and two circumferentially severable portions 76 and 78 defined by housing seams 80 and 82. The hemostatic valve 60 is also shown in a circumferentially separated state so that the valve 60 can also be removed radially.

Specifically, FIG. 16 shows the distal end of an elongated medical device, preferably an anastomosis suturing device 84, inserted through the hemostastic valve 60 and the tube 58 into the vessel lumen 40. With the anastomosis suturing device 84 in position, the two housing portions 76, 78 and two segments 70, 72 of the cannula are separated and withdrawn from the vessel wall 30. Only the anastomosis suturing device 84 remains inserted into the vessel wall 30. The opposite pairs of tubing seams, valve seams, and housing seams are advantageously separated circumferentially to ease their coaxial engagement from the anastomosis suturing device 84 and ease their removal.

The tube 58 provides a working channel for the insertion of many types of medical devices. For example, endoscopes, punches, guide wires and other devices can be inserted while maintaining hemostasis. Furthermore, the tube 58 provides a working channel which is reusable.

The tube 58 is preferably made of an extrudable Teflon. Polyester and polyvinyl chloride are also preferred materials. Other conventional medical polymers are also suitable for use with the present invention. The circumferentially severable tube seams 64, 74 are preferably formed by scoring the polymeric tubing partially through the thickness of the tube wall. The scoring should be sufficient to create a yield point to allow for a controlled, longitudinal break to occur upon application of a circumferential force at the tube seam 64, 74 when the two segments 70, 72 are pulled apart.

Adequate hemostasis is maintained during the procedure of inserting and removing the cannula 14 to leave the anastomosis device 84 at the puncture site 34. The hemostatic valve 60 is shown in further detail in FIGS. 17A and 17B. The hemostatic valve 60 is made up of a circumferential wall 86 which forms an inner valve bore 88 that is adapted to slidably receive the anastomosis device 84 (as illustrated in FIG. 16). The circumferential wall 86 has a circumferentially severable valve seam 90 at a location about its circumference.

The circumferential wall 86 is shown in FIG. 17A to include two leaflets 92, 94 that are radially opposed and face each other. The hemostatic valve 60 is in this configuration when positioned within the tube 58 or housing 62 of the cannula 14. Inner valve bore 88 is formed between the leaflets 92, 94 having a first end portion 96 which form two pairs of confronting circumferential ends, one pair of confronting circumferential ends 98, 100 being secured and the other pair of confronting circumferential ends 102, 104 being severable to form the valve seam 90.

The first end portion 96 of the leaflets 92, 94 when engaged as described, essentially form an annulus of material. The annulus can be contiguous, where the confronting circumferential ends 102, 104 are either secured or are adjacent portions of one continuous piece of material. In the contiguous annulus embodiment, the valve seam 90 includes at least in part of a frangible intersection between circumferential ends 102, 104. The annulus can also be noncontiguous, wherein ends 102, 104 are separated by a break which forms at least a portion of the valve seam 90.

The valve seam 90 preferably runs the longitudinal length of the circumferential wall 86 forming the inner valve bore 88. The hemostatic valve 60 may also include one valve seam such as seam 90, or more than one such valve seam, such as having a first one at valve seam 90 and a second one at valve seam 106. The embodiment of cannula 14 in FIG. 16, for example, includes a hemostatic valve 60 having two valve seams that are shown separated. Preferably, at least-one of the leaflets is secured to the tube 58 or housing 62 in order to be removed from the internally disposed anastomosis device 84.

Each of leaflets 92, 94 also has an opposite second end portion 108 that is adapted to be radially biased into tube 58. The second end portion 108 of each leaflet 92, 94 forms the inner valve bore 88 when in a closed condition. The inwardly biased second end portion 108 is expandable so that the anastomosis device 84 can be slideably received through the inner valve bore 88. In this configuration, the anastomosis device 84 may be advanced through the tube 58 and through inner valve bore 88 such that the inwardly biased second end portion 108 of the leaflets 92, 94 forms a hemostatic seal around the anastomosis device 84.

The hemostatic valve 62 can be made of the same material as the tube 58 or other conventional medial polymer that exhibits some resiliency such as, but not limited to, silicone rubber, silastic tubing, or low modulus polyurethane material. The hemostatic valve 62 is preferably sized to allow for some deformation in its shape while introducing the medical device into the tube 58 while maintaining a hemostatic seal around the medical device.

The housing 62 is shown in more detail in FIGS. 18A–B. The housing 62 includes a housing wall 110 that defines an inner bore 112 forming at least a portion of the tube 58 (as seen in FIG. 16). The inner bore 112 can be adapted to internally engage a hemostatic valve such as valve 60 (FIGS. 17A–B). The housing wall 110 has at least one housing seam 80 and, preferably, a second housing seam 82 that is circumferentially severable.

The housing 62 can also be constructed of a conventional medical polymer of the same type selected for the tube 58 or one having more rigid properties that the material selected for the tube 58. The housing 62 may be formed integrally with the tube 58 or separately and then attached. For example, the housing 62 can be secured to the tube 58 with a suitable adhesive, by heat melting, or using a mechanical interference fit. The attachment of the housing 62 to the tube 58 should be hemostatically sealed.

The operation of the anastomosis device 84 to deploy sutures through a graft 114 (e.g., a segment of saphenous vein) and the tissue surrounding the puncture site 34 in the vessel wall 30 and suture the graft to the vessel wall is shown in FIGS. 19–22. The anastomosis assembly 84 includes a proximal graft suturing device 116, and a distal vessel suturing device 118. Even though the suture devices 116 and 118 are illustrated herein with regard to vascular tissue, it should be understood that the present invention is not limited to any particular type of tissue. The graft suturing device 116 is used to deploy needles 120 with attached sutures radially outwardly through the wall of the graft 114 at a location adjacent an open distal end 122 of the graft. Details of the graft suturing device 116 are shown in FIGS. 26–28C. The vessel suturing device 118 is used to deploy vessel needles 124 with releasably attached sutures proximally through the tissue surrounding the puncture site 34. Details of the structure of the vessel suturing device 118 are shown in FIGS. 24A–C and 25. Although the present invention prefers releasably attaching each suture to one of the needles, a non-releasable attachment between the suture and needle is also contemplated.

Figure 19:
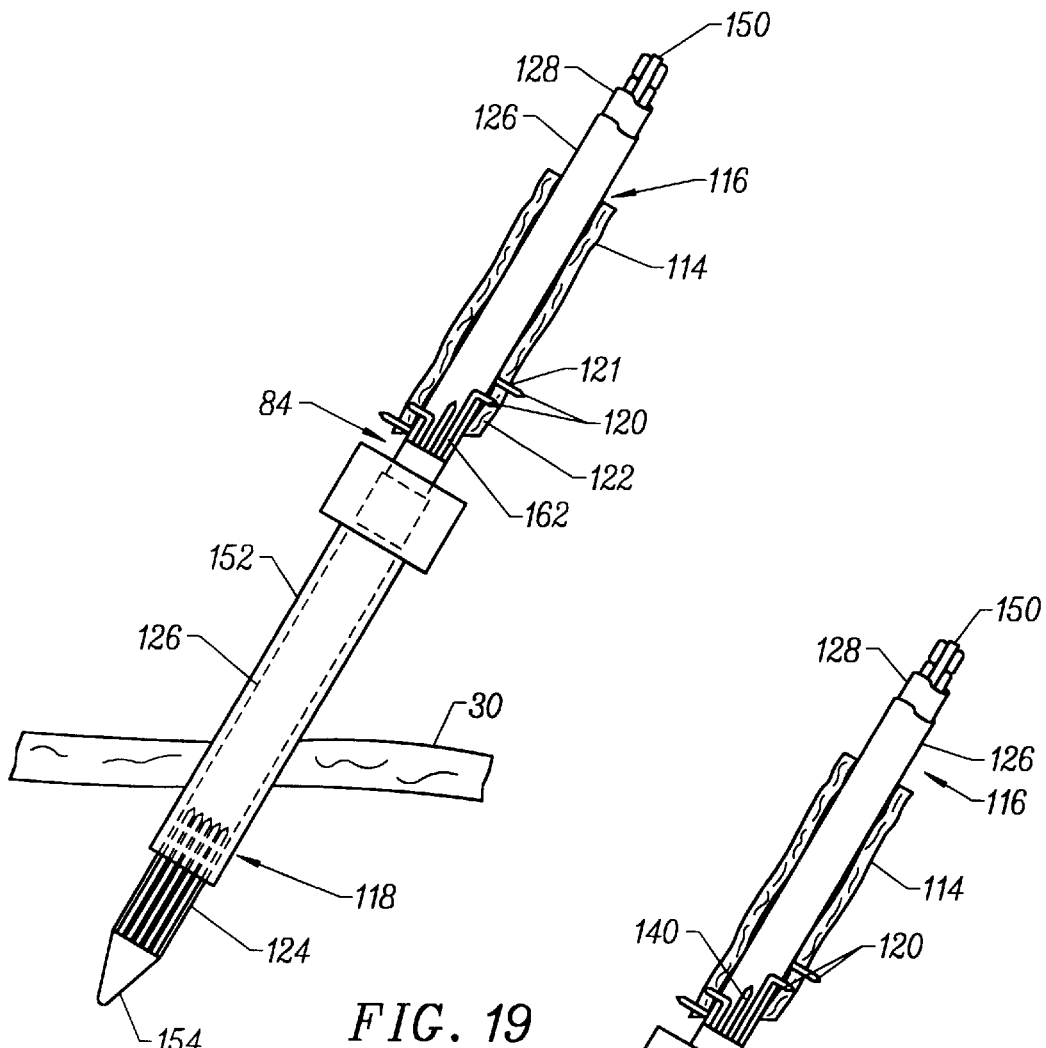
FIGS. 19–22 are elevational views of an anastomosis suturing device of the invention at various stages of its operation.

FIG. 19 shows the graft 114 positioned coaxially about the graft suturing device 116 with needles 120 deployed radially outwardly through the graft 114 in a regularly spaced, oblong pattern of penetration sites 121 or suture ports in the tissue. FIGS. 26–28C more specifically illustrate the details of the graft suturing device 116 that permits such deployment. The graft suturing device 116 includes an outer sleeve 126 and a cylindrical inner hub 128 that is rotatably received coaxially within the outer sleeve 126. In FIG. 26, the distal end of hub 128 has a reduced diameter section 130 that carries a series of axially spaced ribs 132 of the same diameter as the main body 134 of the hub 128. The hub 128 has a multiplicity of circumferentially spaced axial channels 136. The channels 136 extend axially through the ribs 132 and through the main body 134 as shown in FIGS. 26–28C, each channel 136 receives a suture 138, one end of which is attached to one of the needles 120. Any suitable surgical closure materials can be used for the suture 138. The distal end of sleeve 126 has a multiplicity of circumferentially spaced axial slots 140 that register with channels 136. The slots 140 permit the needles 120 to be removed from the device 116 after they have been deployed through the tissue of the vessel wall 30. Each slot 140 terminates proximally in a round opening 142 that forms a needle port through which the tip of one of the needles 120 is radially outwardly extended.

The needles 120 are L-shaped for the sake of illustration and have a sharpened tip 144, a shank 146, and a base 148. The sutures 138 are attached to the base 148 as shown in FIG. 26. As described above, the needles 120 are preferably removably attached to the graft suturing device 116 so that the needle forms the penetration site 121 in the graft and both the needle and suture are passed through the graft 114.

A non-removable attachment between the needle 120 and the graft suturing device 116 is also disclosed by the present invention. In this embodiment, the needle 120 forms the penetration site 121 in the graft 114 and is reversibly withdrawn through the same penetration site. The suture 138 is passed through the penetration site in the graft 114. The suture 138 is detached from the needle 120 at the surface of the graft 114 or after the needle has also partially passed through the penetration site in the graft 114. The needle 120 is retracted into the outer sleeve 126 by the reverse procedure described above.

Figure 20:
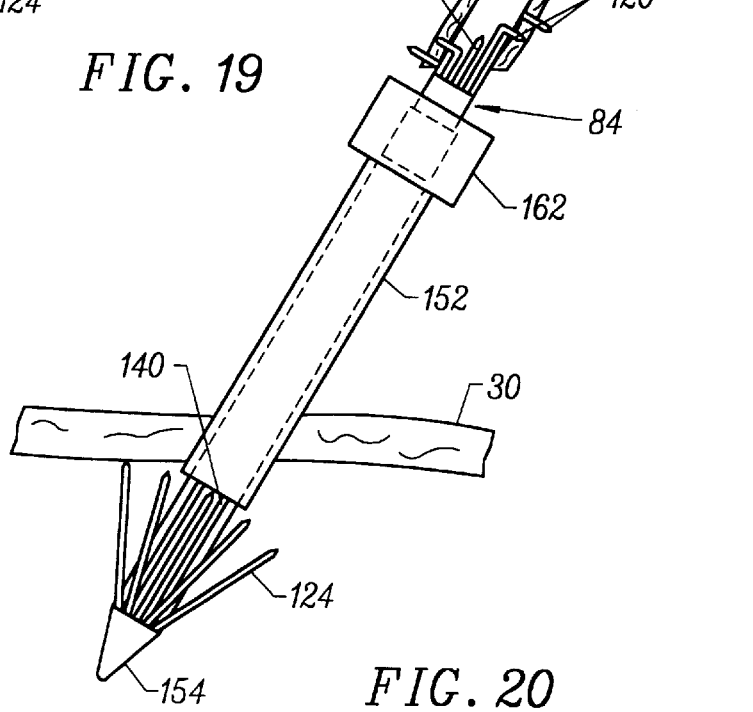
Figure 21:
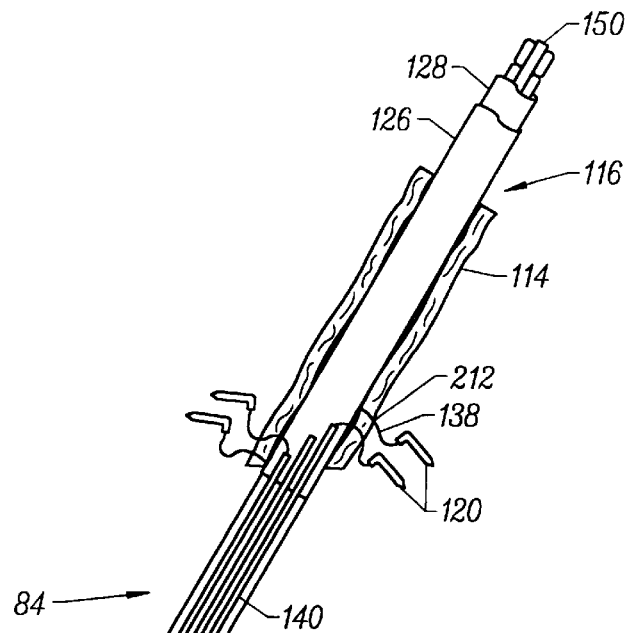

The needles 120 are preferably made of a highly resilient surgical metal, such as a super-elastic metal or memory alloy, for instance a nickel-titanium alloy (commonly called Nitinol alloys). The use of such resilient alloys permits the needles to be elastically deformed when housed within the outer sleeve and spring back to their original shape when passed from beneath the outer sleeve. In the needles 120 retracted position (FIGS. 26 and 28A), the base 148 is positioned axially between adjacent ribs 132, with the shank 146 deformed to extend circumferentially about section 130 of the hub, and with the tip 144 in registry with one of the openings 142. As the hub 128 is rotated within the sleeve 126 by turning the shaft 150, the tips of the needles 120 are projected through openings and radially outwardly at an acute angle relative to normal at the surface of the outer sleeve 126, although in a plane substantially perpendicular to the longitudinal axis of the graft suturing device 116 (FIGS. 26, 28B). Continued rotation of the hub 128 projects the needles 120 further outwardly (FIG. 28C) and thus through the graft 114 that surrounds the exterior of outer sleeve 126 (FIGS. 19 and 20).

FIGS. 19–22 and 24A–25 depict the structure of vessel suturing device 118 that permits deployment of a set of needles 124 around the puncture site 34 in the vessel wall 30 to which the graft 114 is to be sutured. Vessel suturing device 118 generally includes the distal end of sleeve 126 to which the needles 124 are attached and an outer axially slidable tear-away sleeve 152, which can be the cannula 14 described in the previous drawings. The distal end of sleeve 126 has a blunt, cone-shaped distal tip 154 to prevent injury to the interior wall of the vessel. As seen in FIGS. 24A–25, the sleeve 126 also has a plurality of circumferentially spaced radial openings 156 to accommodate the adjacent distal tip 154. The openings 156 are angled proximally to receive the ends of needles 124.

As described above, the needles 124 are preferably removably attached to the vessel suturing device 118 so that each needle forms a penetration site 125 in the vessel wall 30 and both the needle 124 and suture 138 are passed through the vessel wall 30. A non-removable attachment between the needle 124 and the vessel suturing device 118 is also disclosed by the present invention. In this embodiment, the needle 124 forms the penetration site 125 in the vessel wall 30 and is reversibly withdrawn through the same penetration site. The suture 138 is passed through the penetration site in the vessel wall 30. The suture 138 is detached from the needle 124 at the surface of the vessel wall 30 or after the needle has also partially passed through the penetration site 125 in the vessel wall 30. The needle 124 can be retracted into the outer sleeve 126 by using the shaft 150 to proximally pull the distal tip 154 partially over the attached ends of the needles 124 which moves the needles 124 radially toward the shaft 150. Preferably, the needles 124 return to their original position so that the outer sleeve 124 can be advanced over the needles 124 as described in FIG. 19.

The needles 124 are also preferably made of a highly resilient surgical metal, such as a super-elastic metal or memory alloy. The use of such resilient alloys permits the needles to be elastically deformed when housed within the outer sleeve and spring back to their original shape when passed from beneath the distal end of the outer sleeve. Each needle 124 has a sharpened tip 158 and a base 160 to which the other end of one of sutures 138 is affixed. The distal ends of slots 140 open, respectively, into openings 156. When the needles are in their retracted position (FIG. 19), they are received into slots 140. The slots 140 also house the sutures 138 as seen in FIG. 24. The shaft 150 is connected to the tip 154 to permit the barrel to be moved axially relative to sleeve 152. The sleeve 152 has a proximal flange 162 which can be gripped by the physician to move the sleeve axially.

As shown in FIG. 19 the distal end of distal section 154 initially extends into the vessel with sleeve 152 housed coaxially about sleeve 126 to maintain needles 124 in a retracted position. The needles are exposed (FIG. 20) by moving the tip distally or the sleeve proximally (or both) using shaft 150 or flange 162, respectively. Once the sleeve is clear of the needle tips, the needles are free to relax and move radially outwardly as seen in FIG. 20. The needles are then pulled proximally through the tissue surrounding the aperture (FIG. 21) and sleeve 152 is removed.

Figure 22:
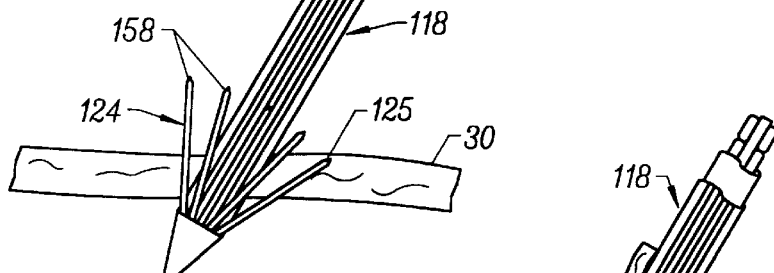
Figure 23:
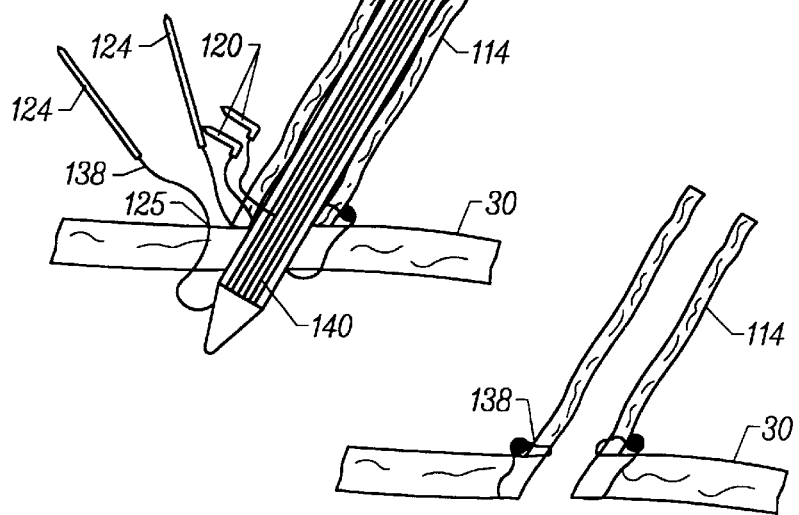
FIG. 23 is a sectional view showing an anastomosis between a tubular graft and a vessel as formed by the anastomosis suturing device of FIGS. 17–20.
Figure 29:
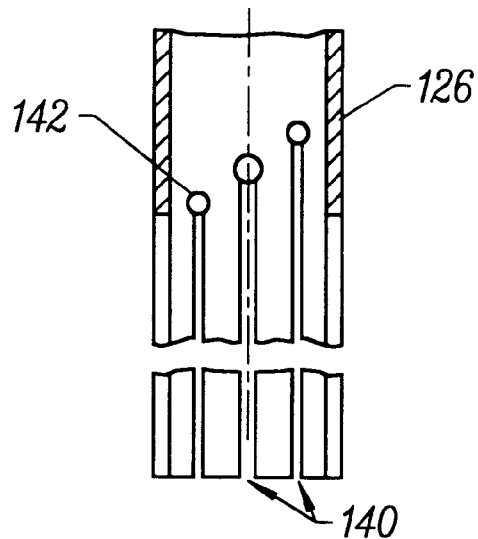
FIG. 29 is a cross sectional view of the graft suturing device showing the slots and openings which receive the needles.
Figure 30:
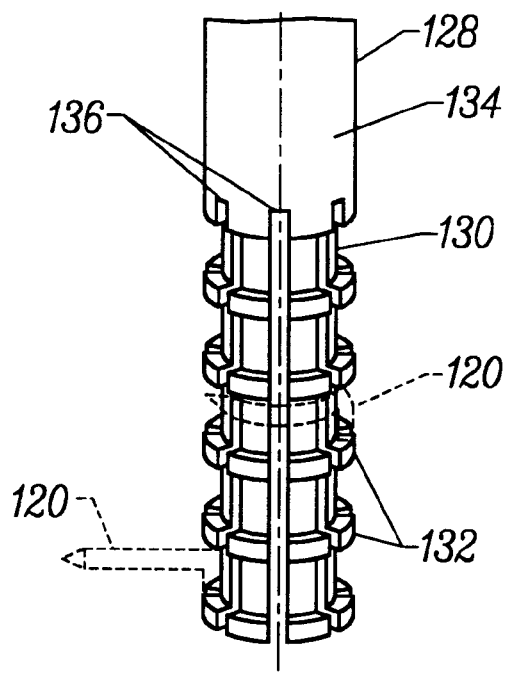
FIG. 30 is a view of the distal end of the graft suturing device.

The needles 120 are pulled through the graft 114 and free of the proximal end of the anastomosis suturing device 84 and the needles 124 are pulled through the vessel tissue and free of the distal end of the device 84. The slots 140 enable the sutures to be released from the device 84. As seen in FIG. 14, the graft 114 is then slid distally from sleeve 126 into contact with the vessel. At this point, the suture extends in a loop from the base of needles 124, through the vessel tissue adjacent the aperture into the graft, and radially outwardly through the graft to the base of needles 120. The needles are then removed from the ends of the sutures, the sutures trimmed to appropriate length, and tied off as shown in FIGS. 22 and 23. The tie-off of the suture ends can be done automatically or with conventional surgical knot tying methods. Optionally, the graft 114 can be clamped off proximally of the anastomosis to maintain hemostasis after the graft has been sutured in place.

The graft suturing device 116 and the vessel suturing device 118 can be used solely independent (one without the other) or operating together simultaneously or successively. Preferably, the graft suturing device 116 can be loaded with the graft 114 prior to the insertion and operation of the vessel suturing device 118. The two devices are then combined into one assembly to provide proper orientation of the graft 114 to the deployed suture pattern in the vessel wall. This results in a two-stroke method being used wherein one needle passes the suture through the graft 114 and a second needle passes the suture through the vessel wall 30.

In another embodiment, a one-stroke method can be used with the present invention. For example, using only the vessel suturing device 118, the needles 124 can first pass the suture through the proximal side of the graft 114 before they are attached to the distal end 154 of the vessel suturing device 118. Then, as described above, the vessel suturing device 118 is inserted through the vessel wall 30. The suture can then be passed through the distal side of the vessel wall 30 to complete the loop.

Generally, the devices of the present invention can be used for suturing all types of tissue in many applications. More specifically, the present invention can close apertures in tissue or bind layers of tissue together such as in anastomoses. For example, and not for limitation, the present invention can be used to close apertures in the septum of the heart such as with a atrial septal defect or a patent foramen ovale. The present invention can deploy sutures around the annulus of a valve for the heart or other organs and around the proximity of a prosthesis.

The present invention can be used in anastomoses to provide a direct or indirect communication between two blood vessels, lymphatics, hollow viscera, or other tubular structures. Although the anastomoses between an aperture in a vessel wall and the end of a graft is specifically illustrated, the present invention can also be used to anastomose tubular structures in other configurations such end-to-end, end-to-side, in continuity, conjoined, or closed-end. Examples of specific applications include the CABG methods described herein using vessels and tubular grafts such as the aorta, veins, the internal mammary artery, or superficial temporal artery. An example of an anastomosis involving an organ instead of a blood vessel is a Roux-en-Y operation which implants the distal end of the divided jejunum with the proximal end into the side of thejejunum at a suitable distance below the first to form a Y-shape pattern.

The present invention can be used with catheter-based surgical techniques wherein one of the elements of the devices described herein is delivered to the suture site through a remote or alternate access location. For example, the vessel suturing device described herein can be introduced to the aorta through the femoral artery to the site where the sutures are deployed.

While particular embodiments of the invention have been herein described in detail, it is to be appreciated that the present invention encompasses variations and combinations thereof, as may be apparent to one of ordinary skill from this disclosure. It is therefore to be understood that within the scope of the appended claims, the invention may be practiced otherwise than as specifically described herein.

What is claimed is:

1. A device for suturing tissue in the proximity of an aperture in a tissue layer, the device comprising:
    a shaft having a proximal end and a distal end;
    at least one needle carried near the distal end of the shaft and adapted to be placed through the aperture, the needle having a shank carried by the shaft and a tip disposed toward the proximal end of the shaft, wherein the needle has a first radially collapsed position that extends proximally along a needle carrying portion, and is adjustable to a second radially expanded position that extends proximally and outwardly from the needle carrying portion; and
    a suture having a first suture portion secured to the needle and a second suture portion extending toward the proximal end of the shaft, the first suture portion being extendible outwardly through the tissue adjacent the aperture by placing the needle through the aperture, proximally withdrawing the needle to thereby puncture the tissue adjacent the aperture with the needle tip, detaching the needle from the shaft, and advancing the needle and first suture portion through the tissue, wherein said first suture portion when extended outwardly through the tissue can be secured with a knot to the second suture portion external of the aperture without substantially obstructing or constricting the aperture.

2. The suturing device of claim 1, wherein the needle is in said first radially collapsed position when radially confined and is radially biased from said first radially collapsed position to said second radially expanded position when radially unconfined.

3. The suturing device of claim 1, wherein the suture comprises a single length of material.

4. The suturing device of claim 1, wherein the distal end of the shaft includes a needle aperture, the needle is positioned within the needle aperture, and the shaft includes a suture lumen that connects to the needle aperture, the suture lumen is adapted to house the second suture portion.

5. The suturing device of claim 1, wherein the distal end of the shaft further includes:
   an occluding body located near the distal end of the shaft and adapted to substantially occlude the aperture to maintain hemostasis at the aperture while the needle and the distal suture end portions attached thereto are placed outwardly through the tissue surrounding the aperture.

6. The suturing device of claim 1, wherein the device includes:
   a plurality of the needle, each of the needles circumferentially spaced about the distal end of the shaft; and
   a plurality of the suture, each of the sutures having its first suture portion secured to a needle and its second suture portion extending toward the proximal end of the shaft.

7. The suturing device of claim 6, wherein the distal end of the shaft further includes a plurality of needle apertures, each of the needles being carried by one of the needle apertures; and the shaft further includes a plurality of suture lumens, each suture lumen connecting to a corresponding one of the needle apertures, each suture lumen adapted to house a corresponding second suture portion.

8. The suturing device of claim 7, wherein the needles have a first radially collapsed position that extends proximally along the body when radially confined, and are adjustable to a second radially expanded position that extends proximally and outwardly of the body when radially unconfined.

9. The suturing device of claim 1 wherein the device further includes:
   at least one pair of needles carried near the distal end of the shaft; and
   the length of suture is secured to and extends between the pair of needles.

10. The suturing device of claim 9 wherein the suture is of sufficient length to be drawn through the tissue on opposite sides of the aperture.

11. The suturing device of claim 10 wherein the suture forms a knot to draw the aperture closed.

12. The suturing device of claim 1 wherein the needle is of sufficient length for drawing the suture through a second tissue layer.

13. The suturing device of claim 12 wherein the suture forms a knot to draw the tissue layer and second tissue layer in contact with one another without closing said aperture.

14. The suturing device of claim 13 wherein the tissue is vascular tissue, the tissue layer defines a vessel wall and the second tissue layer defines a graft.

15. The suturing device of claim 1 wherein the needle is adapted to penetrate vascular tissue and the tissue layer is a vessel wall.

16. A device for suturing vascular tissue in the proximity of an aperture in a vessel wall, the device comprising:
   a shaft having a proximal and distal end, the shaft being adapted for advancing through the aperture;
   at least one needle carried near the distal end of the shaft;
   a length of suture secured to the needle;
   means for drawing the suture through the vascular tissue in the proximity of the aperture; and
   means for maintaining adequate perfusion through the vessel while advancing the distal end of the shaft through the aperture in the vessel wall, drawing the suture through the vascular tissue and securing the suture to the vascular tissue in the proximity of the aperture, the maintaining means and drawing means being integrally formed with the shaft.

17. The suturing device of claim 16 wherein the maintaining means includes maintaining hemostasis in the proximity of the aperture while advancing the shaft through the aperture in the vessel wall, drawing the suture through the vascular tissue and securing the suture to the vascular tissue in the proximity of the aperture.

18. The suturing device of claim 16 wherein the suture is drawn proximally through the vascular tissue from the interior of the vessel.

19. The suturing device of claim 16 wherein the suture is drawn through the aperture and then through the vascular tissue.

20. The suturing device of claim 16 wherein the means for maintaining adequate perfusion includes adapting the shaft to be at least equal in diameter to the aperture.

21. A device for suturing vascular tissue in the proximity of an aperture in a vessel wall, the device comprising:
   a shaft having a proximal and distal end, the shaft being adapted for advancing through the aperture;
   at least one needle carried near the distal end of the shaft;
   a length of suture secured to the needle;
   means for drawing the suture through the vascular tissue in the proximity of the aperture; and
   means for maintaining hemostasis at the aperture while advancing the distal end of the shaft through the aperture in the vessel wall, drawing the suture through the vascular tissue and securing the suture to the vascular tissue in the proximity of the aperture, the maintaining means and drawing means being integrally formed with the shaft.

22. The suturing device of claim 21 wherein the means for maintaining hemostasis includes adapting the shaft to be at least equal in diameter to the aperture.

23. The suturing device of claim 21 wherein the suture is drawn proximally through the vascular tissue from the interior of the vessel.

24. The suturing device of claim 21 wherein the suture is drawn through the aperture and then through the vascular tissue.

25. A graft anastomosis assembly for suturing a tubular graft about an aperture in a tissue wall, the assembly comprising:
   a tissue suturing device having a tissue shaft with a tissue needle carrying portion and a tissue needle being secured to and extending outwardly from the tissue needle carrying portion;
   a graft suturing device having a graft shaft with a graft needle carrying portion and a graft needle being secured to and extending outwardly from the graft needle carrying portion; and
   a suture having a first suture portion secured to the tissue needle and a second suture portion secured to the graft needle, the tissue suturing device being adapted to place the first suture portion proximally from the interior of the tissue wall and through the tissue adjacent the aperture, and the graft suturing device being adapted to place the second suture portion proximally from the interior of the graft and through a wall of the graft, such that the first and second suture portions form a loop which is tightened to secure a portion of the graft to the tissue wall.

26. The graft anastomosis assembly of claim 25, wherein the tissue needle is secured to the tissue needle carrying portion, such that the first suture portion may be placed through the tissue wall by placing the tissue needle carrying portion distally through the aperture, advancing the tissue needle proximally to puncture the tissue adjacent the aperture, detaching the tissue needle from the tissue needle carrying portion, and drawing the tissue needle with the first suture portion engaged therewith outwardly through the tissue wall to allow the first suture portion to be harvested and to retract the tissue needle.

27. The graft anastomosis assembly of claim 25, wherein the graft suturing needle is secured to the graft needle carrying portion, such that the second suture portion may be placed through the graft wall by extending the graft needle outwardly from the graft needle carrying portion and through the graft wall, detaching the graft needle from the graft needle carrying portion, and drawing the graft needle with the second suture portion outwardly through the graft wall to allow the second suture portion to be harvested and to retract the graft needle.

28. The graft anastomosis assembly of claim 25, wherein the tissue needle has a first radially collapsed position that extends proximally along the tissue needle carrying portion and is adjustable to a second radially expanded position wherein it extends proximally and outwardly from the tissue needle carrying portion.

29. The graft anastomosis assembly of claim 28, wherein the tissue needle is in the first radially collapsed position when radially confined, and is biased to relax from the first radially collapsed position to the second radially expanded position when radially unconfined.

30. The graft anastomosis assembly of claim 25, wherein the graft suturing device further includes:
    a tubular sleeve having a wall with a needle port through the wall; and
    a cylindrical inner hub housed coaxially within the tubular sleeve and having a radially recessed groove, the cylindrical inner hub is adjustable relative to the tubular sleeve such that the groove is in registry with the needle port, the graft needle is secured within the groove and is extendible radially outwardly from the shaft of the graft suturing device and through the needle port by adjusting the positioning of the cylindrical inner hub relative to the tubular sleeve.

31. The graft anastomosis assembly of claim 30, wherein the radially recessed groove is a circumferential groove and wherein the graft needle is radially outwardly extendible from the shaft of the graft suturing device through the needle port by rotating, the cylindrical inner hub relative to the tubular sleeve.

32. The graft anastomosis assembly of claim 25, wherein the assembly further includes:
    a plurality of tissue needles spaced circumferentially about the periphery of the tissue needle carrying portion;
    a plurality of graft needles spaced circumferentially about the periphery of the graft needle carrying portion; and
    a plurality of sutures, each suture having a first suture portion secured to one of the tissue needles and a second suture portion secured to one of the graft needles.

33. The graft anastomosis assembly of claim 32, wherein the plurality of graft needles are both circumferentially spaced and longitudinally spaced to form a uniform, predetermined suture pattern about the periphery of the graft needle carrying portion.

34. The graft anastomosis assembly of claim 33, wherein the suture pattern has an oblong shape.

35. The graft anastomosis assembly of claim 25, wherein the tissue suturing device further includes an occluding body on the tissue needle carrying portion and located near the distal end of the tissue shaft, the occluding body is adapted for substantially blocking the aperture, whereby hemostasis is maintained at the aperture.

36. The graft anastomosis assembly of claim 25, wherein the graft suturing device is telescopically engaged with the tissue suturing device.

37. The graft anastomosis assembly of claim 25, wherein the tissue suturing device and the graft suturing device share a common longitudinal axis.

38. The graft anastomosis assembly of claim 25, wherein the assembly maintains hemostasis in the proximity of the aperture.

39. The graft anastomosis assembly of claim 25, wherein the assembly maintains perfusion in the proximity of the aperture.

40. The graft anastomosis assembly of claim 25 the assembly further includes a cannula having a lumen with a hemostatic valve disposed internal of the lumen, the cannula is adapted to advance through the aperture and into the interior of the tissue, the lumen and hemostatic valve are adapted to slideably receive the tissue needle carrying portion while maintaining hemostasis in the proximity of the aperture.

41. The graft anastomosis assembly of claim 40, wherein the cannula includes a tube forming at least a portion of the lumen and having an inner surface, and a tubular wall with a tube seam along a longitudinal axis thereof that is circumferentially severable; and wherein the hemostatic valve includes a circumferential wall forming an inner valve bore, the circumferential wall having a valve seam that is circumferentially severable, whereby the tissue needle carrying portion is removable from coaxial engagement within the lumen by separating the tube seam and the valve seam.

42. The graft anastomosis assembly of claim 25, the assembly further includes a surgical punch having an elongate body and distal end portion with at least one moveable blade adapted for cutting a plug of tissue from the tissue wall to thereby form the aperture, whereby the cannula and hemostatic valve are adapted to be coaxially advanced over the surgical punch and into the interior of the tissue through the aperture, and the surgical punch is removed proximally through the cannula and thereby remove the plug of tissue from the aperture while maintaining hemostasis in the proximity of the aperture with the hemostatic valve.

43. A device for suturing tissue in the proximity of an aperture in a tissue layer, the device comprising:
    a shaft having a proximal end and a distal end, wherein the distal end of the shaft includes a needle aperture, and the shaft includes a suture lumen that connects to the needle aperture;
    at least one needle positioned within the needle aperture and adapted to be placed through the aperture, the needle having a shank carried by the shaft and a tip disposed toward the proximal end of the shaft; and
    a suture having a first suture portion secured to the needle and a second suture portion extending toward the proximal end of the shaft and housed in said suture lumen, the first suture portion being extendible outwardly through the tissue adjacent the aperture by placing the needle through the aperture, proximally withdrawing the needle to thereby puncture the tissue adjacent the aperture with the needle tip, detaching the needle from the shaft, and advancing the needle and first suture portion through the tissue, wherein said first suture portion when extended outwardly through the tissue can be secured to the second suture portion external of the aperture without obstructing or constricting the aperture.

44. The suturing device of claim 43, wherein said at least one needle has a first radially collapsed position that extends proximally along a needle carrying portion of the shaft, and is adjustable to a second radially expanded position that extends proximally and outwardly from the needle carrying portion.

45. The suturing device of claim 43, wherein said at least one needle is in said first radially collapsed position when radially confined and is radially biased from said first radially collapsed position to said second radially expanded position when radially unconfined.

46. The suturing device of claim 43, wherein the suture comprises a single length of material.

47. The suturing device of claim 43, wherein the distal end of the shaft further includes:

an occluding body located near the distal end of the shaft and adapted to substantially occlude the aperture to maintain hemostasis at the aperture while the needle and the distal suture end portions attached thereto are placed outwardly through the tissue surrounding the aperture.

48. The suturing device of claim 43, wherein the device includes:

a plurality of needles, each of the needles circumferentially spaced about the distal end of the shaft; and a plurality of sutures, each of the sutures having its first suture portion secured to a needle and its second suture portion extending toward the proximal end of the shaft.

49. The suturing device of claim 43 wherein the suture is of sufficient length to be drawn through the tissue on opposite sides of the aperture.

50. The suturing device of claim 43 wherein the needle is of sufficient length for drawing the suture through a second tissue layer.

51. The suturing device of claim 50 wherein the suture draws the tissue layer and second tissue layer in contact with one another without closing said aperture.

52. The suturing device of claim 43 wherein the tissue layer comprises a vessel having a vessel wall and further comprising:

means for maintaining adequate perfusion through the vessel while advancing the distal end of the shaft through the aperture in the vessel wall, drawing the suture through the tissue and securing the suture to the tissue in the proximity of the aperture, the maintaining means and drawing means being integrally formed with the shaft.

53. The suturing device of claim 52 wherein the maintaining means includes maintaining hemostasis in the proximity of the aperture while advancing the shaft through the aperture in the vessel wall, drawing the suture through the vessel tissue and securing the suture to the vessel tissue in the proximity of the aperture.

54. The suturing device of claim 43 wherein the means for maintaining hemostasis includes adapting the shaft to be at least equal in diameter to the aperture.

55. A device for suturing tissue in the proximity of an aperture in a tissue layer, the device comprising:

a shaft having a proximal end and a distal end, wherein the distal end of the shaft further includes a plurality of needle apertures and the shaft includes a plurality of suture lumens where each suture lumen connects to one of said needle apertures;

a plurality of needles, each of the needles circumferentially spaced about the distal end of the shaft and adapted to be placed through the aperture and each of the needles being carried by one of the needle apertures, each of said needles having a shank carried by the shaft and a tip disposed toward the proximal end of the shaft; and a plurality of sutures, each of the sutures having its first suture portion secured to a needle and its second suture portion extending toward the proximal end of the shaft and housed within one of said suture lumens, the first suture portion being extendible outwardly through the tissue adjacent the aperture by placing the needle through the aperture, proximally withdrawing the needle to thereby puncture the tissue adjacent the aperture with the needle tip, detaching the needle from the shaft, and advancing the needle and first suture portion through the tissue, wherein said first suture portion when extended outwardly through the tissue can be secured to the second suture portion external of the aperture without obstructing or constricting the aperture.

56. The suturing device of claim 55, wherein said needles have a first radially collapsed position that extends proximally along the shaft when radially confined, and are adjustable to a second radially expanded position that extends proximally and outwardly of the body when radially unconfined.

57. The suturing device of claim 55, wherein the distal end of the shaft further includes:

an occluding body located near the distal end of the shaft and adapted to substantially occlude the aperture to maintain hemostasis at the aperture while said needles and said distal suture end portions attached thereto are placed outwardly through the tissue surrounding the aperture.

58. The suturing device of claim 55 wherein said sutures are of sufficient length to be drawn through the tissue on opposite sides of the aperture.

59. The suturing device of claim 55 wherein said needles are of sufficient length for drawing the suture through a second tissue layer.

60. The suturing device of claim 59 wherein each of said sutures draws the tissue layer and second tissue layer in contact with one another without closing said aperture.

61. The suturing device of claim 55 wherein the tissue layer comprises a vessel wall of a vessel and further comprising:

means for maintaining adequate perfusion through the vessel while advancing the distal end of the shaft through the aperture in the vessel wall, drawing at least one of said sutures through the tissue and securing the suture to the vessel tissue in the proximity of the aperture, the maintaining means and drawing means being integrally formed with the shaft.

62. The suturing device of claim 61 wherein the maintaining means includes maintaining hemostasis in the proximity of the aperture while advancing the shaft through the aperture in the vessel wall, drawing at least one of said sutures through the tissue and securing the suture to the vessel tissue in the proximity of the aperture.

63. The suturing device of claim 61 wherein the means for maintaining hemostasis includes adapting the shaft to be at least equal in diameter to the aperture.

64. The suturing device of claim 61 wherein said at least one needle is in said first radially collapsed position when radially confined and is radially biased from said first radially collapsed position to said second radially expanded position when radially unconfined.

65. The suturing device of claim 61 wherein each of said sutures comprises a single length of material.

66. The suturing device of claim 61 wherein said needles include at least one pair of needles carried near the distal end of the shaft and a length of said sutures secured to and extending between the pair of needles.

* * * * *